United States Patent [19]

Vallee et al.

[11] Patent Number: 5,624,910

[45] Date of Patent: Apr. 29, 1997

[54] METHOD FOR THE INHIBITION OF ALDH-I USEFUL IN THE TREATMENT OF ALCOHOL DEPENDENCE OR ALCOHOL ABUSE

[75] Inventors: Bert L. Vallee, Brookline; Wing-Ming Keung, Wayland, both of Mass.

[73] Assignee: The Endowment for Research in Human Biology, Inc., Boston, Mass.

[21] Appl. No.: 170,272

[22] PCT Filed: Jun. 30, 1992

[86] PCT No.: PCT/US92/05598

§ 371 Date: May 24, 1994

§ 102(e) Date: May 24, 1994

[87] PCT Pub. No.: WO93/00896

PCT Pub. Date: Jan. 21, 1993

Related U.S. Application Data

[63] Continuation-in-part of Ser. No. 723,404, Jul. 1, 1991, Pat. No. 5,204,369.

[51] Int. Cl.$^6$ .................................................. A61K 31/70
[52] U.S. Cl. .................................................. 514/27; 514/811
[58] Field of Search ..................... 514/811, 27; 549/403; 536/8

[56] References Cited

PUBLICATIONS

A. Huntley Blair et al., "Some Catalytic Properties of Human Liver Alcohol Dehydrogenase," 1966, Biochemistry 5: 2026–2034.

Bert L. Vallee, M.D., "Alcohol Metabolism and Metalloenzymes," 1966, Therapeutic Notes 14: 71–74.

William F. Bosron et al., 1977, "Isolation and Characterization of an Anodic Form of Human Liver Alcohol Dehydrogenase," Biochem. Biophys. Res. Comm. 74: 85–91.

William F. Bosron et al., 1979, "Human Liver π–Alcohol Dehydrogenase: Kinetic and Molecular Properties," Biochemistry 18: 1101–1105.

Bosron et al., 1980, "New Molecular Forms of Human Liver Alcohol Dehydrogenase: Isolation and Characterization of ADH (Indianapolis)," Proc. Natl. Acad. Sci. USA 77: 5784–5788.

Parés and Vallee, 1981, "New Human Liver Alcohol Dehydrogenase Forms with Unique Kinetic Characteristics," Biochem. Biophys. Res. Comm. 98, No. 1: 122–130.

Warren E.C. Wacker et al., 1965, "Treatment of Ethylene Glycol Poisoning with Ethyl Alcohol," JAMA 194: 1231–1233.

William A. Frey et al., 1980, "Digitalis Metabolism and Human Liver Alcohol Dehydrogenase," Proc. Natl. Acad. Sci. USA 77: 924–927.

Göran Mårdh et al., 1985, "Human Class I Alcohol Dehydrogenases Catalyze the Oxidation of Glycols in the Metabolism of Norepinephrine," Proc. Natl. Acad. Sci. USA 82: 4979–4982.

Göran Mårdh et al., 1986a, "Testosterone Allosterically Regulates Ethanol Oxidation by Homo– and Heterodimeric γ–Subunit-Containing Isozymes of Human Alcohol Dehydrogenase," Proc. Natl. Acad. Sci. USA 83: 2836–2840.

Valerio Consalvi et al., 1986, "Human Alcohol Dehydrogenases and Serotonin Metabolism," Biochem. Biophys. Res. Comm. 139: 1009–1016.

Göran Mårdh, et al., 1986b, "Human Class I Alcohol Dehydrogenases Catalyze the Interconversion of Alcohols and Aldehydes in the Metabolism of Dopamine," Biochemistry 25: 7279–7282.

Göran Mårdh et al., 1986c, "Human Class II (π) Alcohol Dehydrogenase Has a Redox–Specific Function in Norepinephrine Metabolism," Proc. Natl. Acad. Sci. USA 83: 8908–8912.

Göran Mårdh et al., 1987, "Thyroid Hormones Selectively Modulate Human Alcohol Dehydrogenase Isozyme Catalyzed Ethanol Oxidation," Biochemistry 26: 7585–7588.

Arthur J. McEvily et al., 1988, "3β–Hydroxy–5β–steroid Dehydrogenase Activity of Human Liver Alcohol Dehydrogenase Is Specific to γ–Subunits," Biochemistry 27: 4284–4288.

Wing–Ming Keung, 1991, "Human Liver Alcohol Dehydrogenases Catalyze the Oxidation of the Intermediary Alcohols of the Shunt Pathway of Mevalonate Metabolism," Biochem. Biophys. Res. Comm. 174: 701–707.

Louis G. Lange and Vallee, 1976, "Double–Ternary Complex Affinity Chromatography: Preparation and Alcohol Dehydrogenases," Biochemistry 15: 4681–4686.

Wing–Ming Keung et al., 1985, "Identification of Human Alcohol Dehydrogenase Isozymes by Disc Polyacrylamide Gel Electrophoresis in 7M Urea," Biochem. Biophys. Res. Comm. 151: 92–96.

Philipps Montavon et al., 1989, "A Human Liver Alcohol Dehydrogenase Enzyme–Linked Immunosorbent Assay Method Specific for Class I, II, and III Isozymes," Anal. Biochem. 176: 48–56.

(List continued on next page.)

Primary Examiner—Nicky Chan
Attorney, Agent, or Firm—Banner & Allegretti, Ltd.

[57] ABSTRACT

Method for inhibiting aldehyde dehydrogenase activity using daidzin and/or daidzin analog and/or daidzin or daidzin analog in combination with a factor or factors which increase the bioavailability of the daidzin or daidzin analog, as ALDH-I inhibitory compounds or compositions. Such inhibitory compounds or compositions are useful as pharmaceutical compositions in methods for the treatment of alcohol dependence (i.e., alcoholism) or alcohol abuse, for alcohol sensitization, for extinguishing an alcohol-drinking response, for suppressing an urge for alcohol, for inducing alcohol intolerance, for preventing alcoholism in an individual with or without a susceptibility or predisposition to alcoholism or alcohol abuse, and for limiting alcohol consumption in an individual whether or not genetically predisposed.

6 Claims, 14 Drawing Sheets

OTHER PUBLICATIONS

Jean–Pierre von Wartburg et al., 1964, "Human Liver Alcohol Dehydrogenase. Kinetic and Physicochemical Properties," Biochemistry 3: 1775–1782.

Louis G. Lange et al., 1976, "Human Liver Alcohol Dehydrogenase: Purification, Composition, and Catalytic Features," Biochemistry 15: 4687–4693.

Fred W. Wagner et al., 1983, "Kinetic Properties of Human Alcohol Dehydrogenase: Oxidation of Alcohols by Class I Isoenzymes," Biochemistry 22: 1857–1863.

Fred W. Wagner et al., 1984, "Physical and Enzymatic Properties of a Class III Isozyme of Human Liver Alcohol Dehydrogenase: $\chi$–ADH," Biochemistry 23: 2193–2199.

Charles C. Ditlow et al., 1984, "Physical and Enzymatic Properties of a Class II Alcohol Dehydrogenase Isozyme of Human Liver: $\pi$–ADH," Biochemistry 23: 6363–6368.

Wing Ping Fong, et al., 1987a, "Substrate Specificity of Human Class I Alcohol Dehydrogenase Homo– and Heterodimers Containing the $\beta_2$ (Oriental) Subunits," Biochem. 26: 5726–5732.

Wing Ping Fong, et al., 1987b, "$\beta_2$ (Oriental) Human Liver Alcohol Dehydrogenases Do Not Exhibit Subunit Interaction: Oxidation of Cyclohexanol by Homo– and Heterodimers," Biochem. 26: 5733–5738.

Ting–Kai Li, et al., 1977, "Isolation of Alcohol Dehydrogenase of Human Liver: Is it a Determinant of Alcoholism?," Proc. Natl. Acad. Sci. USA 74: 4378–4381.

Jörnvall et al., 1984, "Human Liver Alcohol Dehydrogenase: Amino Acid Substitution in the $\beta_2\beta_2$ Oriental Isozyme Explains Functional Properties, Establishes an Active Site Structure, and Parallels Mutational Exchanges in the Yeast Enzyme," Proc. Natl. Acad. Sci. USA 81: 3024–3028.

Hedvig von Bahr–Lindström et al., 1986, "cDNA and Protein Structure for the $\alpha$ Subunit of Human Liver Alcohol Dehydrogenase," Biochemistry 25: 2465–2470.

Jan–Olov Höög et al., 1987, "Structure of the Class II Enzyme of Human Liver Alcohol Dehydrogenase: Combined cDNA and Protein Sequence Determination of the $\pi$ Subunit," Biochemistry 26: 1926–1932.

W. P. Fong et al., 1989, "Liver Alcohol and Aldehyde Dehydrogenase Isozymes in a Chinese Population in Hong Kong," Human Heredity 39: 185–191.

Parés et al., 1984, "Organ Specific Alcohol Metabolism: Placental $\chi$–ADH," Biochem. Biophys. Res. Comm. 119: 1047–1055.

Thomas B. Beisswenger et al., 1985, "$\chi$–ADH is the Sole Alcohol Dehydrogenase Isozyme of Mammalian Brains: Implications and Inferences," Proc. Natl. Acad. Sci. USA 82: 8369–8373.

Bert L. Vallee, et al., "Isozymes of Human Liver Alcohol Dehydrogenase," in *Isozymes: Current Topics in Biological and Medical Research*, Rattazzi et al. (eds.) pp. 219–244, Alan R. Liss, Inc., NY, 1983.

Bert L. Vallee, "A Novel Approach to Human Ethanol Metabolism: Isoenzymes of Alcohol Dehydrogenase." Invited Lecture, Proceedings of the 20th International European Brewery Convention, Helsinki, 1985.

Parés et al., 1990, "Class IV Mammalian Alcohol Dehydrogenase," FEBS Lett. 227: 115–118.

Alberto Moreno, et al., 1991, "Purification and Characterization of a New Alcohol Dehydrogenase from Human Stomach," J. Biol. Chem., 266: 1128–1133.

Moyra Smith et al., 1971, "Development Changes and Polymorphism in Human Alcohol Dehydrogenase," Ann. Hum. Genet., Lond., 34: 251–271.

Hans Jörnvall et al., 1987, "Structures of Human Alcohol and Aldehyde Dehydrogenases," Enzyme 37: 5–18.

Regina Pietruszko, "Aldehyde Dehydrogenase (EC 1.2.1.3)" in *Biochemistry and Physiology of Substance Abuse*, Watson (ed.), pp. 89–127, 1989.

H. Werner Goedde et al., 1979, "Racial Difference in Alcohol Sensitivity: A New Hypothesis," Hum. Genet. 51: 331–334.

H. Werner Goedde et al., 1987, "Polymorphism of Aldehyde Dehydrogenase and Alcohol Sensitivity," Enzyme, 37: 29–44.

Akira Yoshida et al., 1984, "Molecular Abnormality of an Inactive Aldehyde Dehydrogenase Variant Commonly Found in Orientals," Proc. Natl. Acad. Sci. USA 81: 258–261.

H. Werner Goedde et al., 1990, "Pharmacogenetics of Aldehyde Dehydrogenase (ALDH)," Pharm. Ther., 45: 345–371.

Tetsuro Ohmori et al., 1986, "The Role of Aldehyde Dehydrogenase Isozyme Variance in Alcohol Sensitivity, Drinking Habits Formation and The Development of Alcoholism in Japan, Taiwan and the Philippines," Prog. Neuro–Psychopharmacol. and Biol. Psychiat., 10: 229–235.

Peter Banys, M.D., 1988, "The Clinical Use of Disulfiram (Antabuse®): A Review," J. Psychoactive Drugs 26: 243–261

E.E. Williams, M.D. 1937, "Effects of Alcohol on Workers with Carbon Disulfide," JAMA 109: 1472–1473.

Allen H. Neims et al., 1966, "A Sensitive Radioassay for Sulfhydryl Groups with Tetraethylthiuram Disulfide*", J. Biol. Chem. 241, pp. 3036–3040.

Curtis Wright, M.D., et al., 1990, "Disulfiram Treatment of Alcoholism," Am. J. Medicine, 88: 647–655.

J. E. Peachey, et al., 1985, "The Role of Drugs in the Treatment of Alcoholism," Medical Progress, May:45–59.

1991 Physician's Desk Reference (Medical Economics Co., Oradell, NJ, Product Information—Antabuse® pp. 2358–2359.

Richard K. Fuller et al., 1986, "Disulfiram Treatment of Alcoholism," JAMA 256: 1449–1455.

Richard W. Fuller et al., 1979, "Disulfiram for the Treatment of Alcoholism," Ann. Int. Med. 90: 901–904.

Edward M. Sellers et al., 1981, "Drugs to Decrease Alcohol Consumption," N. Eng. J. Med. 305: 1255–1262.

John E. Peachey, M.D., et al., 1989a, "Calcium Carbimide in Alcoholism Treatment. Part 1: A Placebo–Controlled, Double–Blind Clinical Trial of Short–Term Efficacy," Brit. J. Addict. 84: 877–887.

J. K. W. Ferguson, M.D., 1956, "A New Drug For Alcoholism Treatment," Canad. M. A. J., 74: 793–795.

Terence M. Reilly, 1976, "Peripheral Neuropathy Associated With Citrated Calcium Carbimide," Lancet (Apr. 24, 1976): 911–912.

Rodd's Chemistry of Carbon Compounds, 1965, vol. 1, Part C, Coffey, ed., Elsevier, Amsterdam, Cyanamide and it Derivatives, p. 374.

Richard A. Deitrich et al., 1976, "Inhibition of Aldehyde Dehydrogenase In Brain and Liver by Cyanamide," Biochem. Pharmacol. 25: 2733–2737.

Eugene G. DeMaster et al., 1982, "Metabolic Activation of Cyanamide By Liver Mitochondria, A Requirement For The Inhibition of Aldehyde Dehydrogenase Enzymes," Biochem. Biophys. Res. Comm. 107: 1333–1339.

Eugene G. DeMaster et al., 1983, "Metabolic Activation of Cyanamide to an Inhibitor of Aldehyde Dehydrogenase in Vitro," Pharmacol. Biochem. Behav. 18 (Suppl. 1): 273–277.

Eugene G. DeMaster et al., 1984, "The Metabolic Activation of Cyanamide to an Inhibitor of Aldehyde Dehydrogenase is Catalyzed By Catalase," Biochem. Biophys. Res. Comm. 122: 358–365.

Gregory W. Svanas et al., 1985, "Enzymatic Requirement For Cyanamide Inactivation of Rat Liver Aldehyde Dehydrogenase," Biochem. Pharmacol. 34: 1197–1204.

F. N. Shirota et al., 1987a, "Metabolism of Cyanamide to Cyanide and An Inhibitor of Aldehyde Dehydrogenase (ALDH) by Rat Liver Microsomes," Alcohol & Alcoholism Supp. 1: 219–223.

F. N. Shirota et al., 1987b, "Cyanide is a product of the Catalase–Mediated Oxidation of the Alcohol Deterrent Agent, Cyanamide," Toxicol. Let. 37: 7–121.

H. T. Nagasawa et al., 1990, "Evidence for Nitroxyl in the Catalase–Mediated Bioactivation of the Alcohol Deterrent Agent Cyanamide," J. Med. Chem. 33: 3120–3122.

Hans Marchner et al., 1983, "Studies in Vitro on the Inactivation of Mitochondrial rat–liver Aldehyde Dehydrogenase by the Alcohol–sensitizing compounds Cyanamide, 1–Aminocyclopropanol and Disulfiram," Biochemical Pharmacology 32: 2181–2188.

John E. Peachey, M.D., 1981, "A Review of the Clinical Disulfiram and Calcium Carbimide in Alcoholism Treatment," J. Clin. Psychopharmacol. 1: 368–375.

S. Valérdiz et al., 1989, "Cyanamide and Its Calcium Form: Do They Differ with Respect to Their Action on the Liver Cell?," Appl. Pathol. 7: 344–349.

L. Conde–Salazar et al., 1981, "Allergic Contact Dermatitis to Cyanamide (Carbodiimide)," Contact Dermatitis 7: 329–330.

J. J. Vázquez et al., 1983a, "Hepatitis Induced by Drugs Used as Alcohol Aversion Therapy," Diagnostic Histopath. 6: 29–37.

J. J. Vézquez et al., 1980, "Cyanamide–Induced Liver Injury in Alcoholics," Lancet 1: 361–362.

Per Thomsen et al., 1981, "Ground Glass Inclusions in Liver Cells in an Alcoholic Treated with Cyanamide (Dipsan)," Liver 1: 67–73.

J. J. Vázquez et al., 1983b, "Cyanamide–Induced Liver Injury. A Predictable Lesion," Liver 3: 225–230.

Miguel Bruguera et al., 1986, "Hepatic Disease Associated with Ground–Glass Inclusions in Hepatocytes After Cyanamide Therapy," Arch. Pathol. Lab. Med. 110: 906–910.

M. Bruguera et al., 1987, "Cyanamide Hepatoxicity. Incidence and Clinico–Pathological Features," Liver 7: 216–222.

W. Rodger, 1962, "Hazards of Calcium Carbimide (Abstem)," Br. Med. J. 2: 989.

Markku Kupari et al., 1982, "Possible Cardiovascular Hazards of the Alcohol–Calcium Carbimide Interaction," J. Toxicol.—Clin. Toxicol. 19: 79–86.

John E. Peachey et al., 1989b, "Calcium Carbimide in Alcoholism Treatment. Part 2: medical findings of a short–term, placebo–controlled, double–blind clinical trial," Brit. J. Addict. 84: 1359–1366.

Zavie W. Brown et al., 1983, "Alcohol–Induced Euphoria Enhanced by Disulfiram and Calcium Carbimide," Alcoholism: Clin. Exp. Res. 7: 276–278.

J. F. Brien et al., 1980, "Intraindividual Variability in the Calcium Carbimide–Ethanol Interaction," Eur. J. Clin. Pharmacol. 18: 199–205.

J.D. Sinclair et al., 1985, "Cyanamide Injections During Alcohol Deprivation Increase Alcohol Drinking," Alcohol 2: 627–630.

Quánguó Zhōngcǎoyào Hulbiān editing group, 1983, Quánguó Zhōngcǎoyào Hulbiān People's Health Publisher, Beijing, pp. 829–830.

Yujiro Niiho et al., 1989, "Pharmacological Studies on Puerariae Flos. (Report No. 1) The Effects of Puerariae Flos on Alcoholic Metabolism and Spontaneous Movement in Mice," Yakugaku Zasshi 109: 424–431.

Fāng Qicheng, 1980, "Some Current Study and Research Approaches Relating To the Use of Plants in the Traditional Chinese Medicine," J. Ethnopharmacol. 2: 57–63.

Shoji Shibata, 1979, "The Chemistry of Chinese Drugs," Amer. J. Chin. Med. 1: 103–141.

Lài and Táng, 1989, Zhōng Guó Zhōng Yào Zá Zhì 14: 308–311.

Yueh and Chu, 1977, "The Metabolic Fate of Daidzein," Scientia Sinica 20: 513–521.

Sū and Zhū, 1979, "The Metabolic Fate of The Effective Components of Radix Puerariae. II. The Absorption, Distribution and Elimination of $^{14}C$–Daidzein," Acta Pharmaceutical Sinica 14: 134 (Abstract).

E. Farmakalidis et al., 1984, "Oestrogenic Response to the CD–1 Mouse to the Soya–Bean Isoflavone Genistein, Genistin and Daidzin," Fd. Chem. Toxic. 22: 237–239.

K. R. Price et al., 1985, "Naturally occurring oestrogens in foods—A Review," Food Add. Contam. 2: 73–106.

Hiromasa Nakamoto et al., 1977, "Study of aqueous extract of Puerariae Radix (report No. $4^1$), Isolation of Daidzin from active extract (MTF–101) of Puerariae Radix and its Antifebrile and Spasmolytic Effects", Yakugaku Zasshi 97: 103–105.

Donald W. Goodwin et al., 1973, "Alcohol Problems in Adoptees Raised Apart From Alcoholic Biological Parents", Arch. Gen. Psychiatry, 28: 238–243.

Robert Langer, 1990, "New Methods of Drug Delivery", Science 249: 1527–1533.

A.K. Ganguly et al., 1970, "Genistein and Daidzein, Metabolites of Micromonospora halophytica", Chemistry and Industry, p. 201.

Yoshimi Kitada et al., 1985, "Analysis of Isolflavones in Puerariae radix by High–Performance Liquid Chromatography with Amperometric Detection", J. Chromatography 347: 438–442.

Mabry et al., 1970, "The Determination and Interpretation of NMR Spectra of Flavonoids", In: The Systematic Identification of Flavonoids, (Mabry et al., eds.), pp. 254–273.

Beeley, 1985, "Analysis of Constituents" In: Laboratory Techniques in Biochemistry and Molecular Biology—Glycoprotein and Proteoglycan Techniques, (Burdon adn van Knippenberg, eds.), pp. 100–152, Elsevier Science Publishers B.V., Amsterdam.

Stahl and Kaltenbach, 1965, "Sugars and Derivatives", In: Thin Layer Chromatography—A Laboratory Handbook, (Stahl, ed.), pp. 461–469, Springer–Verlag, A/P NY).

Wagner et al., 1984, "Flavenoid Drugs", In: Plant Drug Analysis, (Scott trans.), pp. 163–193, Springer–Verlag, Berlin, Heidelberg.

Michiharu Ikawa et al., 1983, "Isolation and Characterization od Aldehyde Dehydrogenase Isozymes from Usual and Atypical Human Livers", J. Biol. Chem. 258: 6282–6287.

Shoji Harada et al., 1980, "Liver Alcohol Dehydrogenase and Aldehyde Dehydrogenase in the Japanese: Isozyme Variation and Its Possible Role in Alcohol Intoxication", Am. J. Hum. Genet. 32: 8–15.

Arthur C. Eldridge et al., 1983, "Soybean Isoflavones: Effect of Environment and Variety on Composition", J. Agric. Food & Chem. 31: 394–396.

Kulkosky et al., 1979, "Free Choice Ethanol Intake and Ethanol Metabolism in Hamster and Rat", Pharmacol. Biochem. & Behav. 11: 439–444.

Computer Search of MARPAT File, Chemical Abstracts "Registry File" and Beilstein File conducted Feb. 16, 1994.

+

ALDH-I

ALDH-II

ORIGIN

−

METHOD FOR THE INHIBITION OF ALDH-I USEFUL IN THE TREATMENT OF ALCOHOL DEPENDENCE OR ALCOHOL ABUSE

This application is a § 371 application of PCT/US92/05598 filed Jun. 30, 1992 which is a continuation-in-part of Ser. No. 07/723,404, filed Jul. 1, 1991, now U.S. Pat. No. 5,204,369.

BACKGROUND OF THE INVENTION

Alcohol abuse and alcohol dependence (i.e., alcoholism) are serious public health problems of modern society. In the United States alone, an estimated 13 million adults exhibit symptoms of alcohol dependence due to excessive alcohol intake, and an additional 7 million abuse alcohol without showing symptoms of dependence according to U.S. Government projections from studies conducted in the mid-1980s. Alcohol dependence and abuse are very expensive: in economic and medical terms, it will cost the U.S. well over $200 billion in 1991 with no prospect of falling or leveling off. The social and psychological damages inflicted on individuals as a consequence of alcohol abuse, e.g., children born with fetal alcohol syndrome (FAS) and victims of alcohol-related accidental death, homicide, suicide, etc., are immense.

While it is generally accepted that alcoholism and alcohol abuse are afflictions with staggering international economic, social, medical, and psychological repercussions, success in preventing or otherwise ameliorating the consequences of these problems has been an elusive goal. Only very recently the public view that alcoholism and alcohol abuse are remediable solely by moral imperatives has been changed to include an awareness of alcoholism and alcohol abuse as physiological aberrations whose etiology may be understood and for which therapy may be found through scientific pursuits. Both alcohol abuse and dependence arise as a result of different, complex, and as yet incompletely understood processes. At present, alcohol research is in the mainstream of scientific efforts.

Our studies on alcohol (ethanol or ethyl alcohol) have been based on the hypothesis that its abuse can ultimately be understood and dealt with at the molecular level. Such a molecular understanding, if achieved, would provide a basis for the identification and development of appropriate therapeutic agents. Our view hypothesizes that the clinical manifestations of alcoholism and alcohol abuse are the consequence of aberrations or defects within one or more metabolic pathways, affected by the presence of ethyl alcohol. In order to test this hypothesis, our initial studies focused on physical, chemical, and enzymatic properties of human alcohol dehydrogenase (ADH), the enzyme that catalyzes alcohol oxidation according to the following reaction formula:

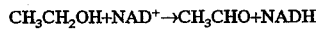

In addition, our studies more recently have focused on the aldehyde dehydrogenases (ALDH) which catalyze the subsequent step in the major pathway of ethanol metabolism according to the following reaction formula:

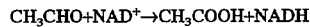

Prior to our research (for example, see Blair and Vallee, 1966, Biochemistry 5:2026-2034), ADH in man was thought to exist in but one or two forms, primarily in the liver, where it was considered the exclusive enzyme for the metabolism of ethanol. Currently, four different classes of ADH encompassing over twenty ADH isozymes have been identified and isolated from human tissues. There is no reason to believe that all of these ADH isozymes are necessary to catalyze the metabolism of a single molecule, ethanol, even though all of them can interact with it. We have proposed that the normal function of these isozymes is to metabolize other types of alcohols that participate in critical, physiologically important processes, and that ethanol interferes with their function (Vallee, 1966, Therapeutic Notes 14:71–74). Further, we predicted that individual differences in alcohol tolerance might well be based on both qualitative and quantitative differences in isozyme endowment (Vallee, 1966, supra).

Our research has established the structures, properties, tissue distribution, and developmental changes for most of the ADH isozymes, which while structurally quite similar, and presumed to have evolved from a common precursor, are functionally remarkably varied. Of the more than 120 publications from our laboratory that relate to the above subjects, the following, arranged in six categories, are especially useful for instruction in the prior art.

(i) *Discovery of isozymes*: Bosron et al., 1977, "Isolation and Characterization of an Anodic Form of Human Liver Alcohol Dehydrogenase," Biochem. Biophys. Res. Comm. 74:85–91; Bosron et al., 1979, "Human Liver π-Alcohol Dehydrogenase: Kinetic and Molecular Properties," Biochemistry 18:1101–1105; Bosron et al., 1980, "New Molecular Forms of Human Liver Alcohol Dehydrogenase: Isolation and Characterization of ADH (Indianapolis)," Proc. Natl. Acad. Sci. USA 77:5784–5788; Parés and Vallee, 1981, "New Human Liver Alcohol Dehydrogenase Forms with Unique Kinetic Characteristics," Biochem. Biophys. Res. Comm. 98, No. 1:122–130.

(ii) *Discovery of new physiological and toxicological substrates*: Wacker et al., 1965, "Treatment of Ethylene Glycol Poisoning with Ethyl Alcohol," JAMA 194:1231–1233; Frey and Vallee, 1980, "Digitalis Metabolism and Human Liver Alcohol Dehydrogenase," Proc. Natl. Acad. Sci. USA 77:924–927; Mardh et al., 1985, "Human Class I Alcohol Dehydrogenases Catalyze the Oxidation of Glycols in the Metabolism of Norepinephrine," Proc. Natl. Acad. Sci. USA 82:4979–4982; Mardh et al 1986a, "Testosterone Allosterically Regulates Ethanol Oxidation by Homo- and Heterodimeric γ-Subunit-Containing Isozymes of Human Alcohol Dehydrogenase," Proc. Natl. Acad. Sci. USA 83:2836–2840; Consalvi et al., 1986, "Human Alcohol Dehydrogenases and Serotonin Metabolism," Biochem. Biophys. Res. Comm. 139:1009–1016; Mardh and Vallee, 1986b, "Human Class I Alcohol Dehydrogenases Catalyze the Interconversion of Alcohols and Aldehydes in the Metabolism of Dopamine," Biochemistry 25:7279–7282; Mardh et al., 1986c, "Human Class II (π) Alcohol Dehydrogenase Has a Redox-Specific Function in Norepinephrine Metabolism," Proc. Natl. Acad. Sci USA 83:8908–8912; Mardh et al., 1987, "Thyroid Hormones Selectively Modulate Human Alcohol Dehydrogenase Isozyme Catalyzed Ethanol Oxidation," Biochemistry 26:7585–7588; McEvily et al., 1988, "3β-Hydroxy-5β-steroid Dehydrogenase Activity of Human Liver Alcohol Dehydrogenase Is Specific to γ-Subunits," Biochemistry 27:4284–4288; Keung, 1991, "Human Liver Alcohol Dehydrogenases Catalyze the Oxidation of the Intermediary Alcohols of the Shunt Pathway of Mevalonate Metabolism," Biochem. Biophys. Res. Comm. 174:701–707.

(iii) *Development of new methods for isolation and characterization*: Lange and Vallee, 1976, "Double-Ternary Complex Affinity Chromatography: Preparation of Alcohol Dehydrogenases," Biochemistry 15:4681–4686; Keung et al., 1985, "Identification of Human Alcohol Dehydrogenase Isozymes by Disc Polyacrylamide Gel Electrophoresis in 7M Urea," Biochem. Biophys. Res. Comm. 151:92–96; Montavon et al., 1989, "A Human Liver Alcohol Dehydrogenase Enzyme-Linked Immunosorbent Assay Specific for Class I, II, and III Isozymes," Anal. Biochem. 176:48–56.

(iv) *Characterization of isozymes*: von Wartburg et al., 1964, "Human Liver Alcohol Dehydrogenase Kinetic and Physicochemical Properties," Biochemistry 3:1775–1782; Blair and Vallee, 1966, supra; Lange et al., 1976, "Human Liver Alcohol Dehydrogenase: Purification, Composition, and Catalytic Features," Biochemistry 15:4687–4693; Wagner et al., 1983, "Kinetic Properties of Human Alcohol Dehydrogenase: Oxidation of Alcohols by Class I Isoenzymes," Biochemistry 22:1857–1863; Wagner et al., 1984, "Physical and Enzymatic Properties of a Class III Isozyme of Human Liver Alcohol Dehydrogenase: $\chi$-ADH," Biochemistry 23:2193–2199; Ditlow et al., 1984, "Physical and Enzymatic Properties of a Class II Alcohol Dehydrogenase Isozyme of Human Liver: $\pi$-ADH," Biochemistry 23:6363–6368; Fong and Keung(a), 1987, "Substrate Specificity of Human Class I Alcohol Dehydrogenase Homo- and Heterodimers Containing the $\beta_2$ (Oriental) Subunits," Biochem. 26:5726–5732; Fong and Keung(b), 1987, "$\beta_2$ (Oriental) Human Liver Alcohol Dehydrogenases Do Not Exhibit Subunit Interaction: Oxidation of Cyclohexanol by Homo- and Heterodimers," Biochem. 26:5733–5738.

(v) *Relationship of isozymes to genetics*: Li et al., 1977, "Isolation of Alcohol Dehydrogenase of Human Liver: Is it a Determinant of Alcoholism?" Proc. Natl. Acad. Sci. USA 74:4378–4381; Jörnvall et al., 1984, "Human Liver Alcohol Dehydrogenase: Amino Acid Substitution in the $\beta_2\beta_2$ Oriental Isozyme Explains Functional Properties, Establishes an Active Site Structure, and Parallels Mutational Exchanges in the Yeast Enzyme," Proc. Natl. Acad. Sci. USA 81:3024–3028; von Bahr-Lindström et al., 1986, "cDNA and Protein Structure for the $\alpha$ Subunit of Human Liver Alcohol Dehydrogenase," Biochemistry 25:2465–2470; Höög et al., 1987, "Structure of the Class II Enzyme of Human Liver Alcohol Dehydrogenase: Combined cDNA and Protein Sequence Determination of the $\pi$ Subunit," Biochemistry 26:1926–1932; Fong et al., 1989, "Liver Alcohol and Aldehyde Dehydrogenase Isozymes in a Chinese Population in Hong Kong," Human Heredity 39:185–191.

(vi) *Tissue distribution of isozymes*: Parés et al., 1984, "Organ Specific Alcohol Metabolism: Placental $\chi$-ADH," Biochem. Biophys. Res. Comm. 119:1047–1055; Beisswenger et al., 1985, "$\chi$-ADH is the Sole Alcohol Dehydrogenase Isozyme of Mammalian Brains: Implications and Inferences," Proc. Natl. Acad. Sci. USA 82:8369–8373.

One ADH isozyme, class III or $\chi$-ADH, is the only one present in brain, placenta, and testis and is least capable of oxidizing ethanol (Parés and Vallee, 1981, supra; Parés et al., 1984, Supra; Beisswenger et al., 1985, supra). As a consequence, these tissues would seem to he at greatest risk with respect to the effects of ethanol. On the other hand, this circumstance also affords these tissues protection from acetaldehyde, the highly toxic oxidation product of ADH.

Alcohol abuse and alcoholism are problems unique to humans. It may not be surprising, therefore, that the complexity in other species is significantly less than in man. Such species differences extend to the catalytic preferences of ADH isozymes toward different alcohols. For example, horse ADH does not oxidize methyl alcohol and ethylene glycol while human ADH does (von Wartburg et al., 1964, supra). Large doses of ethanol administered to compete with methanol or ethylene glycol and prevent their oxidation to toxic products now constitutes the therapy for individuals poisoned with these agents (Wacker et al., 1965, supra). As a consequence of the detailed research exemplified above, much more is known about human ADH than the corresponding enzyme in other species, a unique situation quite the opposite for most other enzymes.

Each of the human ADHs is composed of two protein subunits that form a dimeric molecule. Class I ADHs are made up of $\alpha$, $\beta$, and $\gamma$ subunits which combine into homodimeric and heterodimeric isozymes; class II, III and IV appear to be only homodimers (Vallee and Bazzone, in *Isozymes: Current Topics in Biological and Medical Research*, Rattazzi et al. (eds.) pp. 219–244, Alan R. Liss, Inc., N.Y., 1983; Vallee, B. L., *A Novel Approach to Human Ethanol Metabolism: Isoenzymes of Alcohol Dehydrogenase*. Invited Lecture, Proceedings of the 20th International European Brewery Convention, Helsinki, 1985; Parés et al., 1990, FEBS Lett. 227:115–118). The activities of the different ADHs toward several types of substrates has been examined and is quite revealing (see, for example, Vallee, 1985, supra). Class I isozymes containing at least one $\gamma$-subunit are active toward specific steroid hormones and are selectively inhibited by testosterone (Mårdh et al., 1986a, supra; McEvily et al., 1988, Supra). Class II ADH contains the $\pi$-subunit and is the only one that acts selectively on intermediates in the metabolism of norepinephrine, a critical endocrine and neurotransmitter agent (Mårdh et al., 1986c, supra). The class III ($\chi$) enzyme and its unique characteristics were mentioned above. The recently discovered human class IV ADH (Moreno and Parés, 1991, J. Biol. Chem., 266:1128–1133), found mainly in gastric mucosa, shares the general physicochemical properties of all mammalian ADHs. Kinetically, it resembles class II ADH but is chemically distinct. Since ethanol concentration in the stomachs of drinkers may be as high as 1 to 10M transiently, the moderately high $K_m$, 41 mM, of this isozyme is nevertheless ample to allow it to have a possibly important role in the first pass metabolism of ethanol. Many alcohols other than ethanol have important physiological roles and some are likely to be substrates for one or another of the ADH isozymes. Clearly, the interference of ethanol with normal metabolic processes could have serious consequences, both acute and chronic. One of the main goals of continued research is the identification of these critical substrates.

Genetic subvariants of the $\beta$ and $\gamma$-subunits of ADH isozymes within the general population ($\beta_1$, $\beta_2$, $\beta_3$, and $\gamma_1$, $\gamma_2$) produce characteristic differences in individuals. The first genetic difference found between the form predominant in Caucasians ($\beta_1$) and that predominant in Asians ($\beta_2$) is also the most profound (Smith et al., 1971, Ann. Hum.

Genet., Lond., 34:251–271; Fukui and Wakasugi, 1972, Jpn. J. Leg. Med., 26:46–51); the $\beta_1$-subunit is 100-times less effective in converting ethanol to acetaldehyde than is the $\beta_2$-subunit. All of the differences are now known to result from point mutations at widely different positions in the chain, e.g., $\beta_1 \rightarrow \beta_2$, R47H; $\beta_1 \rightarrow \beta_3$, R369C; $\gamma_1 \rightarrow \gamma_2$, I349V and R271Q but all affect coenzyme binding (Jörnvall et al., 1987, Enzyme 37:5–18). Several population studies have documented striking differences in $\beta_1$ and $\beta_2$ frequencies among Asian and Caucasian populations. For example, in an Asian population in Hong Kong, the $\beta_1$ form of the $\gamma$-subunit was present in only about 10% of the subjects; all others had the $\beta_2$ form (Fong et al., 1989, supra). In contrast, studies on a Caucasian population in England indicated that 90% had the $\beta_1$ form and only 10% had the $\beta_2$ form (Smith et al., 1971, supra).

Aldehyde dehydrogenase (ALDH) is the enzyme that catalyzes the second step in the ethanol metabolic pathway (see reaction formula above). As with ADH, there are multiple forms of ALDH, but only two of these have been examined in any detail; very much less is known about the others. The first two classes, in particular, are thought to have primary responsibility for oxidizing acetaldehyde (Pietruszko, in *Biochemistry and Physiology of Substance Abuse*, Watson (ed.), pp. 89–127, 1989). ALDH-I is present in mitochondria, has a high affinity for acetaldehyde, and has been assigned the major role in acetaldehyde detoxification. ALDH-II, on the other hand, occurs in the cytosol and has a low affinity for acetaldehyde. It is therefore thought to be less effective in its detoxification. The amino acid sequences of both forms are now known (Jörnvall et al., 1987, supra).

An important inactive dominant mutant form of ALDH-I was discovered by Goedde et al., 1979, Hum. Genet. 51:331–334, and shown to be present in approximately 50% of major Asian populations, e.g., Chinese, Japanese and Vietnamese (Goedde and Agarwal, 1987, Enzyme, 37:29–44). This mutant protein apparently results from at least one point mutation (K487E) (Yoshida et al., 1984, Proc. Natl. Acad. Sci. USA 81:258–261) that abolishes enzymatic activity and therefore markedly impairs the ability of heterozygous and homozygous individuals (Goedde and Agarwal, 1990, Pharm. Ther., 95:345–371) to metabolize a variety of aldehydes including acetaldehyde and presumably including any physiologically important aldehydes that are in the range of the specificity characteristic of native ALDH-I. Remarkably, such individuals do not display any pathologic abnormalities but do experience a sensitivity reaction when they consume alcohol. The characteristic facial flushing is the symptom of this reaction that is recognizable immediately. Still more remarkably, this mutation seems to have survival value: alcoholism and alcohol abuse virtually do not exist among Asian flushers (Ohmori et al., 1986, Prog. Neuro-Psychopharmacol. and Biol. Psychiat., 10:229–235).

The Hong Kong study (Fong et al., 1989, supra) documents, for the first time, the joint distribution of the β-ADH and ALDH-I genetic subvariants in a Chinese population. The subvariants classify into four measurably distinct subgroups: 2.2% $\beta_1$-ADH and active ALDH-I; 5.6% $\beta_1$-ADH and inactive ALDH-I; 44.4% $\beta_2$-ADH and active ALDH-I; and 47.8% $\beta_2$-ADH and inactive ALDH-I. Based on the catalytic capacities of the four phenotype varieties, one would expect subjects with $\beta_2$-ADH and inactive ALDH-I to be the most rapidly intolerant of alcohol; those with $\beta_1$-ADH and inactive ALDH-I to be intolerant of alcohol but with less rapid onset; those with $\beta_2$-ADH and active ALDH-I to be moderately tolerant; and subjects with $\beta_1$-ADH and active ALDH-I, i.e., the predominant Caucasian type, to be tolerant.

Since the lack of ALDH-I is not known to generate other significant metabolic problems, save those which are the consequence of ethanol metabolism, it would be ideal if a drug could be found which mimics the effect of this natural genetic variant but without producing substantial toxic side effects; such a drug would clearly offer great promise for the treatment of alcoholism and alcohol abuse.

The experience of Asian flushers with alcohol is not described as "aversion," but rather as intolerance, i.e., as an inability to endure alcohol. This is an important distinction because in Western medicine the psychological setting surrounding the administration of the toxic drugs disulfiram and carbimide has been given considerable emphasis in producing a regimen leading to so-called "aversion therapy" and more recently "psychological deterrence" (Banys, 1988, J. Psychoactive Drugs 26:243–261).

We now describe in detail two types of treatments for alcoholism and alcohol abuse that were known long before either the enzymology or genetics of ADH and ALDH isozymes were known. Their discovery and use has been phenomenological: not based on modern rational drug discovery or design. On the one hand, Western medicine has used toxic chemicals, not further developed since discovery of their effects on exposed industrial workers decades ago, to produce sensitization to alcohol. Ancient Traditional Chinese medicine, on the other hand, has used herbal preparations to treat diseases generally, and in particular alcohol intoxication, according to a philosophy in which herbal mixtures modulate bodily functions; treatment with herbal combinations is highly individualistic both with respect to the practitioner's preferences and prescriptions for the patient; record-keeping is rare; and practice of the art is heavily influenced by oral anecdotal tradition.

The only two pharmaceuticals currently used as alcohol-sensitizing drugs are both chemically reactive species but differently so, both non-specific inhibitors and individually distinct and hence different from one another, and both shown after decades of testing and use to be toxic, unsafe and ineffective. The pharmacological basis for the action of these drugs, disulfiram and carbimide (hereinafter referred to by its chemical name, cyanamide) is thought to be inhibition of hepatic ALDHs, but neither one is selective for ALDH-I, the only ALDH known to be affected by genetic mutation.

Disulfiram

Disulfiram (tetraethylthiuram disulfide) was first proposed as an aversive agent for the treatment of alcoholism by Williams, 1937, JAMA 109:1472–1473. He had noticed that workers in the rubber industry who had been exposed to thiuram compounds, which are used as accelerators of vulcanization, experienced unpleasant effects after consumption of alcohol. Its approved use as a drug dates from 1948.

As to chemical properties, disulfiram is a general reagent for the determination of SH groups in proteins (Neims et al., 1966, J. Biol. Chem. 241, pp. 3036–3040), and reacts with thiols to form the diethylammonium diethyldithiocarbamates, carbon disulfide and the disulfide derived from the thiol (Coffey, supra, pp. 331–332); it undergoes disulfide exchange reactions under mild conditions.

Given its chemical properties, it is not surprising to find that disulfiram is a broadly acting but non-specific inhibitor of many physiologically important sulfhydryl-containing compounds including enzymes, Wright and Moore, 1990, Am. J. Medicine, 88:647–655 (for a review, see Banys, 1988, supra). Thus, it inhibits enzymes critical in neurotransmitter metabolism (dopamine-β-hydroxylase), drug metabolism and detoxification (microsomal mixed function oxidases), and multiple pathways of intermediary metabolism. It is a potent inhibitor of many liver enzymes, including ALDH, DBH, aniline hydroxylase, nicotinamide-adenine dinucleotide phosphate (NADPH) oxidase, and cytochrome P-450. Other studies have demonstrated inhibition of glyceraldehyde-3-phosphate dehydrogenase, succinic dehydrogenase, xanthine oxidase, hexokinase, and NADPH dehydrogenase. Still other studies have established inhibition of superoxide dismutase, which is thought to be an important antioxidant defense mechanism against free radical-induced biological damage. The details of these and other instances of enzyme inhibition may be found in the references cited in Banys, 1988, supra. This lack of specificity clearly contributes to and may be largely responsible for the substantial toxicity that accompanies the therapeutic use of disulfiram.

In vitro, disulfiram (Pietruszko, 1989, supra) is a potent inhibitor of the high $K_m$ cytosolic isozyme (ALDH-II) but inhibits the major acetaldehyde oxidizing mitochondrial isozyme (ALDH-I) only slightly. However, under conditions where trace amounts of certain mercaptans such as 2-mercaptoethanol or the in vivo metabolite methanethiol are added to disulfiram to generate a mixed disulfide, the low $K_m$ mitochondrial ALDH-I isozyme, normally resistant to disulfiram, is inactivated. Thus, disulfiram directly inhibits ALDH-II, but only indirectly inhibits ALDH-I via metabolites (Pietruszko, 1989, supra).

In vivo, disulfiram acts slowly to inhibit ALDH over 12 hours, and this inhibition is irreversible (Pietruszko, 1989, supra). Restoration of ALDH activity after disulfiram administration depends upon de novo enzyme synthesis of ALDH, which requires 6 or more days. Thus, disulfiram and its metabolites have the capacity to shut down hepatic acetaldehyde oxidation via ALDH-I and ALDH-II so that in the presence of high concentrations of ethanol, high levels of acetaldehyde will rapidly accumulate. Although exogenous acetaldehyde is known to be toxic, it is not at all clear that endogenous accumulation of acetaldehyde is the only or even the main causative agent in the so-called disulfiram-alcohol reaction (DAR) described below. The direct involvement of acetaldehyde in any of the manifestations of alcohol intolerance is poorly studied, poorly understood and remains unproven.

Disulfiram is essentially the only alcohol-sensitizing agent approved and marketed for use in the U.S. by Wyeth-Ayerst as Antabuse® and has been used in alcohol-aversion and psychological deterrence therapy. In a patient who has consumed ethanol, inhibition of ALDH by disulfiram produces highly unpleasant physiological reactions, among them flushing, tachypnoea, palpitations, nausea and tachycardia (Peachey and Naranjo, 1985, Medical Progress, May:45–59). The rationale for treatment with disulfiram is that fear of these reactions will deter alcoholics from further drinking (Peachey and Naranjo, 1985, supra).

As described in the 1991 Physician's Desk Reference (Medical Economics Co., Oradell, N.J., pp. 2358–59), Antabuse® plus alcohol, even small amounts, produces flushing, throbbing in the head and neck, throbbing headache, respiratory difficulty, nausea, copious vomiting, sweating, thirst, chest pain, palpitation, dyspnea, hyperventilation, tachycardia, hypotension, syncope, marked uneasiness, weakness, vertigo, blurred vision, and confusion (Physician's Desk Reference, 1991, supra). Significant cardiac, hepatic, and neurological toxicity, have been observed associated with disulfiram therapy. For example, in severe reactions to Antabuse®, there may be respiratory depression, cardiovascular collapse, arrhythmias, myocardial infarction, acute congestive heart failure, unconsciousness, convulsions, and death (see Physician's Desk Reference, supra). These at best undesirable side effects have been attributed to inhibition of enzymes other than ALDHs, as well as inhibition of the normal physiological functions of one or more of the ALDHs. In fact, the risk of taking disulfiram is so high in the minds of many that many clinicians refuse to use this drug to deal with alcohol abuse. Moreover, many patients themselves either refuse to take it or abandon its use. Thus, the art has not yet been provided with a drug for the selective or direct reversible inhibition of ALDH-I without the undesirable side effects or toxicity which accompanies disulfiram treatment.

In fact, placebo-controlled clinical trials of Antabuse® (disulfiram) (Fuller et al., 1986, JAMA 256:1449–1455; Fuller and Roth, 1979, Ann. Int. Med. 90:901–904) have shown that disulfiram is no more effective than the placebo control in reducing alcohol consumption, when compared with pre-treatment levels. According to Banys, 1988, supra, although since 1948 millions of doses of disulfiram have been prescribed for the treatment of alcoholism, well-controlled studies have never demonstrated that disulfiram is more effective than placebos in producing sustained abstinence; most of the studies published in the ensuing 40 years suffer from serious flaws. In reviewing the efficacy of disulfiram, Banys, 1988, supra supports the contention of Sellers et al., 1981, N. Eng. J. Med. 305:1255–1262, that "evidence supporting the efficacy of disulfiram is limited. Controlled clinical trials of efficacy show no improvement or short-term improvement only. Appreciable improvements (abstinence and improved social functioning) reported by chronic alcoholics during the first three months of treatment with therapeutic doses (250 mg daily) and non-therapeutic doses (1 mg daily) probably result from non-specific, non-pharmacologic activity of the drug. The subsequent decline from early improvement after the first three months of treatment probably reflects both the low potency of the drug and the increased importance of nonpharmacologic factors as determinants of long-term outcomes of treatment.

In accord with this, of all the numerous studies of disulfiram, according to Peachey et al.(a), 1989, Brit. J. Addict. 84:877–887, only two properly controlled clinical trials were conducted, and the more recent of these two reported that disulfiram was no more effective than placebos in bringing about continued abstinence in alcoholic patients.

Thus, the weight of the evidence after more than fifty years of use is that disulfiram is not only toxic and unsafe but ineffective.

Cyanamide

The citrated calcium salt of cyanamide was introduced as a result of the search for an alcohol-sensitizing agent less toxic than disulfiram (Ferguson, 1956, Canad. M. A. J., 74:793–795; Reilly, 1976, Lancet (Apr. 24, 1976): 911–912), but even now only disulfiram has been approved for use in the United States. Citrated calcium cyanamide is hydrolyzed to free cyanamide ($H_2NCN$) in aqueous solution, hence the general properties of cyanamide are relevant. Like disulfiram, cyanamide's alcohol-sensitizing effect was discovered among industrial workers exposed to the substance in the workplace. Although chemically distinct from disulfiram, it is also a reactive species. Cyanamide, which readily forms compounds by addition to the cyano group, yields guanidinium compounds, O-alkylisoureas and S-alkylisothioureas when reacted with alkyl amines, alcohols and thiols, respectively (Rodd's Chemistry of Carbon Compounds, 1965, Vol. 1, Part C, Coffey, ed., Elsevier, Amsterdam, p.374), i.e., with the nucleophilic functionalities that are present in proteins. It is so reactive that at slightly alkaline pH it dimerizes to cyanoguanidine, a species that is itself reactive toward nucleophiles, e.g., alkyl amines (Rodd, 1965, supra, p. 349). Incorporation of citrate in the pharmaceutical formulation provides the slightly acid pH required for stability with respect to dimerization.

Neither ALDH-I (the low $K_m$ isozyme) nor ALDH-II (the high $K_m$ isozyme) are inhibited in vitro by cyanamide, but in vivo a reactive product of cyanamide catabolism inhibits both isozymes (Deitrich et al., 1976, Biochem. Pharmacol. 25:2733–2737; DeMaster et al., 1982, Biochem. Biophys. Res. Comm. 107:1333–1339). Formation of this active inhibitor was shown initially to be catalyzed by enzyme(s) present in intact mitochondria and the microsomal fraction of rat liver (DeMaster et al., 1983, Pharmacol. Biochem. Behav. 18 (Supp. 1): 273–277). More recently, mitochondrial catalase has been shown to activate cyanamide to an ALDH inhibitor (DeMaster et al., 1984, Biochem. Biophys. Res. Comm. 122:358–365; Svanas and Weiner, 1985, Biochem. Pharmacol. 34:1197–1204). Further, Shirota et al.(a), 1987, Alcohol & Alcoholism Supp. 1:219–223 and Shirota et al.(b), 1987, Toxicol. Let. 37:7–12, showed that cyanamide inhibits ALDH via a reactive species and that cyanide is generated as a product of cyanamide oxidation by catalase under conditions in which the ALDH inhibitory species is also generated. According to Shirota et al.(b), 1987, supra, this cyanide formation could serve as a basis for cyanamide toxicity in vivo. It was postulated in 1987 (Shirota et al.(b), 1987, supra) that the oxidation of cyanamide would yield nitroxyl (HNO) as a product and that this highly reactive substance is the active ALDH inhibitory species. In 1990, Nagasawa et al. (J. Med. Chem. 33:3120–3122) presented evidence, via isotope tracer experiments, that nitroxyl was formed in the catalase-mediated bioactivation of cyanamide. They suggest that their data and those of others support nitroxyl as the active ALDH inhibitor, noting that millimolar concentrations of cyanide do not inhibit ALDH. Marchner and Tottmar, 1978, Acta Pharmacol. et Toxicol. 43: 219, have reported that inhibition of ALDH with cyanamide is maximal at 1–2 hours after drug administration and is reversible, with restoration of 80% of the ALDH activity occurring within 24 hours.

As with disulfiram, cyanamide has been used in alcohol-aversion and psychological deterrence therapy as described above (Peachey and Naranjo, 1985, supra). According to Peachey, 1981, J. Clin. Psychopharmacol. 1:368–375, cyanamide has not been approved in the United States because of its significant antithyroid activity in experimental animals. Citrated calcium cyanamide is marketed in other countries as Temposil®, Dipsan® and Abstem® (Shirota et al.(a), 1987, supra). "Plain" cyanamide, commonly used in Spain, is marketed as Colme® (Valérdiz and Vázquez, 1989, Appl. Pathol. 7:344–349).

Cyanamide like disulfiram is reported to be associated with medical complications, again as might be expected from its chemical reactivity. Although fewer side effects have been reported with cyanamide than with disulfiram, cyanamide has been studied much less intensively and the information on this drug, including its side effects, especially those which are long-term, is incomplete.

There are a number of known contraindications to treatment with cyanamide. Among the toxic effects of cyanamide reported are the following: (i) allergic contact dermatitis according to Conde-Salazar et al., 1981, Contact Dermatitis 7:329–330 and references cited therein and peripheral neuropathy (also associated with disulfiram) according to Reilly, 1976, supra, who suggests that both cyanamide and disulfiram are general metabolic poisons and may lead to the accumulation of toxic derivatives of chemicals normally metabolized by oxidative pathways; (ii) liver injury, including generation of ground-glass inclusion bodies in liver cells of alcoholics treated with cyanamide (but not disulfiram, Vázquez et al.(a), 1983, Diagnostic Histopath. 6:29–37) as first reported by Vázquez and Cervera, 1980, Lancet 1:361–362 using plain cyanamide and by Thomsen and Reinicke, 1981, Liver 1:67–73 as well as Koyama et al., 1984, Acta Hepatol. Jpn. 25:251–256 using the citrated calcium salt of cyanamide; a series of reports of hepatotoxicity, including ground-glass inclusions, inflammatory reactions associated with liver cell destruction, portal tract fibrosis that can be severe if treatment has been prolonged, scarring, even cirrhosis according to the above-cited references and Vázquez et al.(a), 1983, supra; Vázquez et al.(b), 1983, Liver 3:225–230; Bruguera et al., 1986, Arch. Pathol. Lab. Med. 110:906–910; Bruguera et al., 1987, Liver 7:216–222; Valérdiz and Vázquez, 1989, supra, for cyanamide and disulfiram but not calcium cyanamide; and (iii) cardiotoxic effects, including hypotension and even cardiac death according to Rodger, 1962, Br. Med. J. 2:989 and hazardous cardioacceleration according to Kupari et al., 1982, J. Toxicol. - Clin. Toxicol. 19:79–86; Kupari et al., 1982, supra suggest that the use of alcohol aversive drugs including disulfiram and cyanamide has been contraindicated to patients with known cardiac diseases, but point out that it is common that asymptomatic chronic alcoholics have a number of cardiac problems. Clearly, therefore such drugs may be hazardous.

Peachey et al.(b), 1989, Brit. J. Addict. 84:1359–1366, have conducted the only placebo-controlled, double-blind clinical trial of Temposil®. From this short-term trial, Peachey and his colleagues concluded that this drug was safe for use in alcoholics with normal thyroid function and without other serious medical conditions. Thyroid function was not altered during the short-term trial by Temposil® in patients with normal pretreatment thyroid function. However, in the trial one patient whose baseline thyroid function was decreased became hypothyroid after administration of Temposil®; thus it was concluded that for short-term use in alcoholics with normal thyroid function, the drug was safe. Peachey et al.(a), 1989, supra, report that they did not observe hepatotoxicity as measured merely by blood alkaline phosphatase. Liver biopsies were not performed, so that an assessment of histopathological liver changes in biopsies, such as those cited above with reference to hepatotoxicity of cyanamide, was not done. Despite the premature conclusion of safety by Peachey et al.(a), 1989, supra, as limited by their assessment of what was measured as short-term effects, the effects of long-term treatment with cyanamide in controlled studies is still unknown.

According to Peachey, 1981, supra, in Canada and other countries, cyanamide has not been used widely because of its short duration of activity and its questionable efficacy in reducing drinking. Unfortunately, placebo-controlled clinical trials of Temposil® (chemical name: calcium cyanamide; generic name: calcium carbimide) (Peachey et al.(a), 1989, supra; Peachey et al.(b), 1989, supra) have shown that, compared with pre-treatment levels, cyanamide is only as effective as the placebo control in reducing alcohol consumption.

The weight of the evidence is that cyanamide in its various forms, like disulfiram, is not only toxic and unsafe but ineffective.

There are some reports that use of either disulfiram or cyanamide is counterproductive in treatment of alcoholism. In a double-blind study in humans, consumption of low doses of alcohol together with either disulfiram or cyanamide, induces and enhances euphoria (Brown et al., 1983, Alcoholism: Clin. Exp. Res. 7:276–278). Brien et al., 1980, Eur. J. Clin. Pharmacol. 18:199–205, have reported that their results with male alcoholic volunteers ingesting small amounts of ethanol after oral administration of cyanamide support the self-reports of alcoholics who state that they can circumvent a severe disulfiram-ethanol reaction by ingesting ethanol over a few hours, and thereafter drink excessively with impunity, the so-called burn-off phenomenon. If both disulfiram and cyanamide can be effectively burned-off by slow ingestion for a period followed by excessive consumption without aversion, the effectiveness of these so-called anti-alcohol drugs not only may be severely limited but even generally counterproductive.

Cyanamide has also been shown to have the undesirable effect of actually causing an increase in alcohol consumption in animals given cyanamide after alcohol deprivation (Sinclair and Gribble, 1985, Alcohol 7:627–630). Typically cyanamide is given to alcoholics after they have been withdrawn from alcohol and are being abstinent. According to Sinclair and Gribble, 1985, supra, if this results in a potentiation of the desire for alcohol subsequent to termination of the drug, as appears to be the case in rat experiments, treatment with cyanamide would be counterproductive and should be dropped from usage altogether.

Traditional Chinese Herbal Medicine

Since ancient times, Radix Puerariae (RP), prepared from the root of *Pueraria lobata* Ohwi or Pueraria pseudo-hirsuta Tang et Wang (Leguminosae) and Puerariae Flos (FP), prepared from the flower of *Pueraria lobata* Ohwi have been known for their use in Traditional Chinese medicine. The crude drug RP was described in the first Chinese Materia Medica about 200 B.C. as something of a panacea: an antipyretic, antidiarrhetic, diaphoretic, anti-emetic agent, and, in today's parlance, a general anti-microbial agent. S ūn Sĭmiăo reported the use of RP for the relief of drunkenness in his work "Bèijí-Qiānjīn-Yàofāng" about 600 A.D. Presently, RP is widely used by the Chinese for the treatment of drunkenness, muscle clonus and tonus and myalgia, hypertension, migraine, angina, arrhythmia, and febrile diseases in general (Quánguó Zhōngcăoyào Huìbiān editing group, pp. 829–830, Quánguó Zhōngcăoyào Huìbiān People's Health Publisher, Beijing, 1983). It has been applied also to treat symptoms of febrile illness including chills, and is administered as a root decoction, whose principal use was based on its diaphoretic, antipyretic and spasmolytic effects, according to Niiho et al., 1989, Yakugaku Zasshi 109:424–431 (English translation). According to Niiho et al., 1989, supra, RP is prescribed as a flower decoction to "activate the stomach, stop the thirst and relieve alcohol intoxication," and is believed to have an effect on alcohol elimination.

Although RP has been a part of Chinese medical practice for more than 2000 years, only in the past several decades have attempts been made to purify and classify its active ingredients (see, for example, Fang, 1980, J. Ethnopharmacol. 2:57–63 and references cited therein, including Fang et al., 1974, Zhōng Huá Yī Xué Zá Zhì (Chinese Medical Journal) 5:271–274; Chén and Zhāng, 1985, Zhōng Yào T ōng Bào 10:34–36; Shibata, 1979, Amer. J. Chin. Med. 1:103–141).

RP is a complex mixture with a multiplicity of components, only some few of which have been identified. Besides starch major constituents include daidzein, daidzin, puerarin, genistein, 6,7-dimethoxycoumarin, formononetin, β-sitosterol, allantoin and 5-methylhydantoin. The only pharmacological activities of crude RP which have been studied are its effects on smooth muscle and cerebrovascular and cardiovascular systems. In this regard puerarin is the primary active constituent examined for this purpose (for a review, see Lài and Táng, 1989, Zhōng Guó Zhōng Yàao Z á Zhì 14:308–311; see also, Fang, 1980, supra).

Daidzein has been examined regarding its metabolic fate, but not with regard to any human pharmacological effectiveness, disease state or body system. It is metabolized rapidly, with a half-life on the order of one hour, after intravenous administration to mice (Yueh and Chu, 1977, Scientia Sinica 20:513–521; Sū and Zhū, 1979, Acta Pharmaceutical Sinica 14:134 (Abstract)); an experiment in which daidzein was administered to two human volunteers revealed only that little daidzein had appeared in urine and feces after 60 hours. With this exception, the metabolic fate of daidzein in humans remains unknown. Similarly there is very little knowledge about the effects of crude RP or its constituents on acute or chronic alcohol intoxication.

With respect to daidzin, the only reported pharmacological activity is its estrogenic activity at high doses (Farmakalidis and Murphy, 1984, Fd. Chem. Toxic. 22:237–239; Price and Fenwick, 1985, Food Add. Contam. 2:73–106); daidzin administered subcutaneously in propylene glycol showed no antifebrile (hypothermic) effect in rats and showed no spasmolytic effect in mice (Nakamoto et al., 1977, Yakugaku Zasshi 97:103–105). Thus, the art has not yet identified any components of RP or their activities in the metabolism of ethanol and/or the mediation of the behavioral effects of ethanol. Further, to increase ethanol elimination, RP has been employed in Traditional Chinese medicine in order to relieve or remedy excess alcohol consumption. With respect to ethanol metabolism via ADH and ALDH, this would suggest that components of RP would activate, not inhibit, ADH and ALDH to eliminate consumed ethanol more rapidly. Unexpectedly, we have found ADH-inhibitory compounds in RP. Such compounds, and methods for their use in the treatment of drug-alcohol reactions, have been described and claimed by us in co-pending and co-assigned U.S. application Ser. Nos. 07/724,213 and 07/723,945 filed Jul. 1, 1991, hereby incorporated by reference in their entirety.

In the present invention, a hitherto completely unknown inhibitor of ALDH has been unexpectedly identified and purified from RP. This inhibitor is daidzin, a compound which selectively inhibits the activity of ALDH-I. Daidzin is a potent, yet reversible, inhibitor of ALDH-I, the enzyme whose mutation and resultant inactivation in about 50% of all Chinese, Japanese, Vietnamese and yet other Orientals results in their avoidance of ethanol and correlates with the virtual non-existence of alcoholism in this group (Ohmori et al., 1986, supra). Hence it is useful in the treatment and prevention of alcoholism and alcohol abuse. Daidzin's activity mimics the effect of the naturally occurring ALDH-I genetic variant found among the Chinese. Daidzin selectively inhibits the low $K_m$ ALDH isozyme, hence in its presence high levels of acetaldehyde are likely oxidized via the high $K_m$ isozyme (ALDH-II). This suggests that in the presence of daidzin the accumulation of acetaldehyde will be limited to non-toxic levels by ALDH-II, in contrast to the high levels of acetaldehyde that accumulate with disulfiram which inhibits both ALDH-I and ALDH-II. RP, from which daidzin was isolated, has been used safely and effectively in Traditional Chinese Medicine for two thousand years in a number of medical conditions. Jointly these facts suggest that daidzin would be a direct, safe, effective and reversible agent to induce alcohol intolerance, but without significant toxic side effects which have been consistently observed in the treatment of alcohol abuse with the chemically-reactive and toxic disulfiram and cyanamide. Daidzin's properties as a selective, reversible and potent inhibitor of ALDH-I, while unexpected, are virtually ideal for a compound intended to promote alcohol intolerance and avoidance of its abuse, as is observed in the genetic condition which its use mimics. Even structurally closely related chemical compounds failed to mimic daidzin's selectivity for ALDH-I and remarkable potency as an ALDH inhibitor (see Tables IV and V). Prunetin and genistin were the only other naturally-occurring compounds of those tested which selectively inhibited ALDH-I but was nearly an order of magnitude less potent as an inhibitor than daidzin. In fact, daidzin is the first reversible inhibitor of any ALDH described so far with such high effectiveness and selectivity. Identification of other compounds that may act in concert with daidzin or modify daidzin such that its bioavailability is increased in vivo would be particularly advantageous. Bioavailability refers to the in vivo availability of a compound (e.g., to effect its intended function, for example, as an inhibitor or suppressor of drinking behavior) and can be measured in a variety of ways, for example, by quantitating the amount of compound circulating in the blood relative to the amount administered. For daidzin, the bioavailability has been unexpectedly found to be increased by a factor in RP. The bioavailability of an ALDH-inhibitory analog of daidzin by such factor may be similarly increased.

Daidzein, the aglycone of daidzin which is also present in RP, not only does not inhibit ALDH but instead selectively inhibits certain ADH isozymes. Hence, daidzein inhibits the first but not the second step in human ethanol metabolism, while daidzin inhibits the second but not the first step in human ethanol metabolism as described above. It cannot be predicted so far on strict structural or other grounds which flavone/isoflavone compound present in RP, or any closely related compound, will inhibit ADH or a selective isozyme of ADH, ALDH or a selective isozyme of ALDH, both ADH and ALDH, or neither ADH or ALDH. For example, improved inhibitory compounds may be obtained by synthetic derivatives (i.e., analogs) of daidzin, wherein the glucose is replaced with a different sugar moiety. For example, L and D aldo- or keto-tetroses, pentoses, hexoses, heptoses or the amino, alcohol and/or acid derivatives of such tetroses, pentoses, hexoses or heptoses; or wherein the glucose is replaced by the deoxy analogs of such tetroses, pentoses, hexoses or heptoses. Alternatively, the glucose (GlcO) moiety of daidzin may be replaced by alkoxy or acyloxy groups at the 7-position bearing various chain lengths, for example, up to 11 or more, comprising any of straight chain alkyl, peptidic, polyether, etc. backbones, and the backbones may be substituted with various neutral (e.g., hydroxyl, sugar, etc.) or charged (e.g., carboxylate, phosphate, phosphonate, sulfate, sulfonate, etc.) moieties. Additionally suitable moieties (e.g., carboxylate, hydroxyl, etc.) may be esterified.

These examples are not exhaustive in scope but suggest to those skilled in the art routes to the identification of daidzin derivatives (i.e., analogs) having increased bioavailability and improved potency, selectivity, controlled release, solubility, absorbability and/or stability.

SUMMARY OF THE INVENTION

Figure 1:
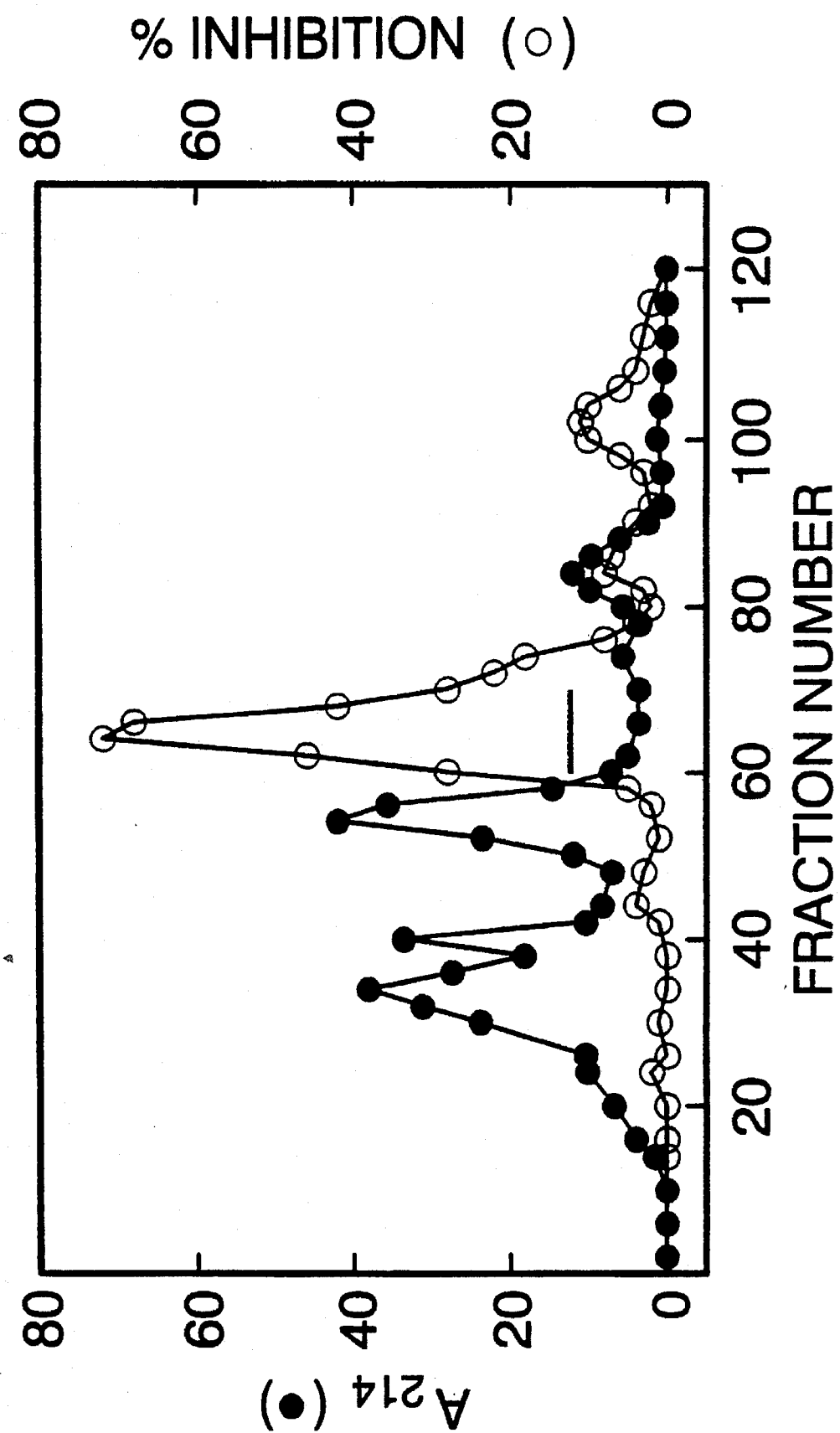
FIG. 1 is a graph of a BioGel P-4 elution profile of RP extract. Fractions containing ALDH inhibitory materials, indicated by the horizontal bar, were pooled and lyophilized.

The invention relates to the inhibition of aldehyde dehydrogenase, the enzyme system which is responsible for the second step in the major pathway of ethanol metabolism in humans, using daidzin or a similar ALDH-inhibiting compound, such as a synthetic analog of daidzin. In the first step, alcohol dehydrogenase (ADH) isozymes catalyze the conversion of ethanol to acetaldehyde. In the second step, aldehyde dehydrogenase (ALDH) isozymes catalyze the conversion of acetaldehyde to acetate. $NAD^+$ is a cofactor in both steps.

More particularly, the invention relates to a method for inhibiting ALDH activity using daidzin or daidzin analog as the inhibitor. Daidzin has been unexpectedly found to be a hitherto unknown, direct, highly potent yet selective, inhibitor of ALDH-I; the inhibition is reversible. In fact it is the first such inhibitor of any ALDH described so far. Daidzin analogs have been prepared which exhibit similar direct, highly potent, but somewhat less selective, ALDH-inhibitory properties. As such, daidzin is useful in a method for the treatment of alcohol dependence (i.e., alcoholism) or alcohol abuse. It is also useful in a method of alcohol sensitization. Daidzin is useful in a pharmaceutical composition for inducing alcohol intolerance in humans. The existing drug disulfiram, said to be alcohol-sensitizing or anti-alcohol, directly inhibits ALDH-II but not ALDH-I, has numerous toxic side effects and has been said widely to be ineffective. Nevertheless, disulfiram is the only alcohol-sensitizing drug currently approved for use in the U.S. (Antabuse®). Disulfiram is a highly-reactive chemical species which inhibits ALDH irreversibly, and in addition, inhibits other non-ALDH enzyme systems in neurotransmitter metabolism, drug metabolism and detoxification, and multiple pathways of intermediary metabolism. This lack of specificity clearly contributes to and probably is the basis of the toxicity that accompanies its use. The other existing alcohol-sensitizing drug, not approved for use in the U.S., is cyanamide, which is also a highly reactive chemical species. Cyanamide is unable to inhibit ALDH isozymes directly in vitro but must be bioactivated in vivo to an ALDH-inhibiting species. This species appears to inhibit both ALDH-I and ALDH-II. The inhibition of ALDH via cyanamide is reported to be reversible and the activity to be of short duration. In contrast to both disulfiram and cyanamide, the present invention provides daidzin a new inhibitor which directly, selectively and reversibly inhibits ALDH-I activity. The present invention additionally provides daidzin analogs as ALDH-I inhibitors.

The invention encompasses compounds of the formula:

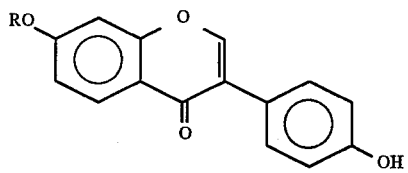

wherein:

R represents straight chain alkyl having 1–11 carbon atoms, or branched chain alkyl having 1–30 carbon atoms, where the branched chain alkyl comprises a straight chain alkyl portion having 1–11 carbon atoms substituted with straight or branched chain lower alkyl groups having 1–6 carbon atoms;

hydroxyalkyl where the alkyl portion is straight chain alkyl having 2–11 carbon atoms, or branched chain alkyl having 2–30 carbon atoms, where the branched chain alkyl comprises a straight chain alkyl portion having 2–11 carbon atoms substituted with straight or branched chain lower alkyl groups having 1–6 carbon atoms;

carboxyalkyl where the alkyl portion is straight chain alkyl having 2–11 carbon atoms, or branched chain alkyl having 2–30 carbon atoms, where the branched chain alkyl comprises a straight chain alkyl portion having 2–11 carbon atoms substituted with straight or branched chain lower alkyl groups having 1–6 carbon atoms; or

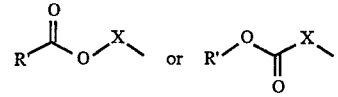

where

X is straight chain alkylene having 2–11 carbon atoms, or branched chain alkylene having 2–30 carbon atoms, where the branched chain alkylene comprise a straight chain alkylene portion having 2–11 carbon atoms substituted with straight or branched chain lower alkyl groups having 1–6 carbon atoms; and R' is straight or branched alkyl having 1–6 carbon atoms.

The invention also encompasses compounds of the formula:

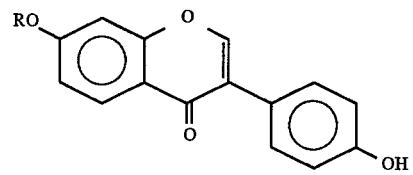

wherein:

R represents straight or branched chain alkyl having 1–11 carbon atoms;

hydroxyalkyl where the alkyl portion is straight or branched alkyl having 2–11 carbon atoms; carboxyalkyl where the alkyl portion is straight or branched alkyl having 2–11 carbon atoms; or

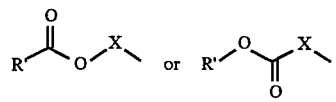

where

X is straight or branched chain alkylene having 2–11 carbon atoms; and

R' is straight or branched alkyl having 1–6 carbon atoms.

By lower alkyl in the present invention is meant straight or branched chain alkyl groups having 1–6 carbon atoms, such as, for example, methyl, ethyl, propyl, isopropyl, n-butyl, isobutyl, tert-butyl, pentyl, 2-pentyl, isopentyl, neopentyl, hexyl, 2-hexyl, 3-hexyl, and 3-methylpentyl.

By alkyl in the present invention is meant (i) straight chain alkyl groups having 1–11 carbon atoms, such as, for example, methyl, ethyl, propyl, n-butyl, pentyl, hexyl, heptyl, octyl, nonyl, decyl, and undecyl, or (ii) branched chain alkyl groups having 1–30 carbon atoms comprising a straight chain alkyl portion having 1–11 carbon atoms substituted with straight or branched chain lower alkyl groups having 1–6 carbon atoms. Examples of such branched chain alkyl groups are 4-n-butyl-undecane, 5-ethylnonane, 4-ethyl-5-isobutyl-5-methyldecane, 3-propyl-4-ethyloctane, and 4-isooctyl-3-propylundecane.

By hydroxyalkyl is meant an alkyl group substituted with a hydroxy moiety at any available position of the alkyl group. Representative hydroxyalkyl groups are, for example, hydroxyethyl, hydroxymethyl, hydroxyhexyl, hydroxypentyl, and hydroxydecyl. In addition, the alkyl groups may be substituted with more than one hydroxy moiety, i.e., the hydroxyalkyl may be a polyhydroxyalkyl group.

By carboxyalkyl is meant radicals of the structure:

where Y represents straight or branched chain alkylene having 1–11 carbon atoms.

In addition the alkyl groups may be substituted with more than one carboxy moiety, i.e., the carboxyalkyl may be a polycarboxyalkyl group.

Furthermore, the alkyl groups may be substituted with one or more hydroxy substituents and one or more carboxy substituents. The hydroxy and carboxy substituents may also be esterified using, respectively, short chain (1–6 carbon atoms) acids and alcohols.

The inhibitor, daidzin, was isolated and purified from Radix Puerariae (RP), a dried root of *Pueraria lobata* which has been in use in Traditional Chinese Herbal Medicine without any reports of toxic side effects for more than two millennia. Daidzin's inhibitory activity mimics the effect of a natural genetic mutation of ALDH-I whose effect is inactive ALDH-I. It is observed in 50% of all Chinese, Japanese, Vietnamese and others (Goedde and Agarwal, 1987, supra). These facts suggest that treatment with daidzin is a safe, effective and reversible means to achieve alcohol intolerance, without the significant toxic side effects associated with known alcohol-sensitizing drugs.

It should be emphasized that all treatment, in the case of RP for two millennia, in the case of disulfiram for 43 and cyanamide for 35 years was empirical, phenomenological and without a known or even suspected biochemical, pharmacological or genetic basis. Among these agents only RP failed to be accompanied by any known toxicity. None of the treatments benefited from the recent progress and current state of relevant scientific disciplines, i.e., in genetics, biochemistry, pharmacology or toxicology. Our isolation of daidzin and recognition of its inhibitory ALDH-I characteristics for the first time instead make use of that knowledge both to recognize its biological and pharmacological properties as well as other effects and to monitor its effectiveness by biochemical assays with ALDH-I and -II and ADH-I through -IV. These properties and assays were unknown at the time that disulfiram and cyanamide were described or tested.

The invention was made possible by several discoveries. First, we have discovered a previously unknown inhibitor of ALDH. We have further discovered that this inhibitor is unexpectedly potent, yet selective for ALDH-I, and at the same time the inhibitory effects are direct yet reversible. No other inhibitors of similar selectivity and potency were discovered in RP, nor in the testing of many other closely related chemical compounds, nor in fact among other compounds. Second, we have demonstrated that an extract containing daidzin, as well as purified daidzin, in the absence of other inhibitors of ALDH, has significant in vivo effects on alcohol consumption in an animal model. More recently, we have discovered that daidzin analogs, with inhibitory properties which mimic daidzin, may be synthesized and used to inhibit ALDH-I. Such daidzin analogs are potent and even when somewhat less selective for ALDH-I than daidzin, the analogs have similar significant in vivo effects on alcohol consumption in the animal model. Additionally, we have discovered that the bioavailability of daidzin administered as a crude extract is increased by 5–10 fold as compared with the bioavailability of daidzin administered as a purified (e.g., synthetic) compound. Therefore, the invention includes a composition of matter that comprises purified (e.g., synthetic) daidzin or a similarly acting daidzin analog and a bioavailability-increasing factor or factors from an extract of RP.

Thus, daidzin or a daidzin analog with inhibitory properties which mimic daidzin is useful in a pharmaceutical composition and in a method for extinguishing an alcohol-drinking response, and in a method for suppressing an urge for alcohol. In addition, daidzin or a daidzin analog with inhibitory properties which mimic daidzin is useful in a pharmaceutical composition and in a method for inducing alcohol intolerance or in a method of preventing alcoholism in an individual with a susceptibility to alcoholism or alcohol abuse or in a method for limiting alcohol consumption in an individual whether or not genetically predisposed.

DETAILED DESCRIPTION OF THE INVENTION

The invention relates to inhibitors of aldehyde dehydrogenase, the enzyme system in humans that is responsible for the second step in the major pathway of ethanol metabolism. The invention further relates to novel synthetic inhibitory compounds that are daidzin analogs. Still further, the invention relates to factors which potentiate the activity of the inhibitory compounds in vivo by significantly increasing the bioavailability of an inhibitory compound, such as daidzin. The invention ecompasses a method for inhibiting ALDH-I activity using daidzin and/or daidzin analog and/or daidzin or daidzin analog in combination with a factor or factors which increase the bioavailability of the daidzin or daidzin analog and pharmaceutical compositions comprising daidzin and/or daidzin analog and/ or daidzin or daidzin analog in combination with a factor or factors which increase the bioavailability of the daidzin or daidzin analog as inhibitor.

In particular, daidzin has been unexpectedly found to be a direct, potent yet selective and reversible inhibitor of ALDH-I. As such, daidzin is particularly useful as a pharmaceutical composition in methods for the treatment of alcoholism or alcohol abuse, for alcohol sensitization, for extinguishing an alcohol-drinking response, for suppressing an urge for alcohol, for inducing alcohol intolerance, and for preventing alcoholism in an individual with or without susceptibility to alcoholism or alcohol abuse, or for limiting alcohol consumption in an individual whether or not genetically predisposed.

Alcoholism (i.e., alcohol dependence) and alcohol abuse are serious public health problems as described in the Seventh Special Report to the U.S. Congress on Alcohol and Health From the Secretary of Health and Human Services January 1990, "Alcohol and Health—An Overview." Two distinct forms of problem drinking were identified in this report—alcohol abuse, which is defined as involving patterns of heavy alcohol intake in nondependent persons in which health consequences and/or impairment in social functioning are associated, and alcohol dependence (i.e., alcoholism), which is differentiated from alcohol abuse on the basis of such manifestations as craving, tolerance, and physical dependence that result in changes in the importance of drinking in one's life and in impairment of the ability to exercise restraint over drinking. There is no consensus on specific definitions of alcoholism, alcoholics or the like. We view the U.S. Government report and definitions as useful to indicate the magnitude of the problem. That report, however, appears to have strayed, in the direction of classification without having the benefit of adequate verification by the medical profession, away from the seminal approach of Goodwin et al., 1973, Arch. Gen. Psychiatry, 28:238–243, in which a genetic link to alcoholism is demonstrated with Danish adoptees where one parent had a hospital diagnosis of alcoholism. We prefer to use a concise paraphrase of the more extensive criteria for drinking categories of Goodwin et al., 1973, supra: non-alcoholic drinkers display at most occasional and illtimed drunkenness; those afflicted with alcoholism display excessive ethanol consumption exceeding dietary and caloric needs or norms which is consequently detrimental to interpersonal, economic and professional effectiveness. Thus, the development of safe and effective drugs for the treatment of alcohol abuse and alcohol dependence are urgently needed to help to solve these serious health problems which are world wide.

According to the present invention, daidzin was isolated and purified from Radix Puerariae (RP), a dried root of Pueraria lobata which has been used safely for 2 millennia in Chinese herbal medicine. Recently, a genetic mutation in ALDH-I has been identified in a subpopulation of Oriental individuals which results in an ALDH-I isozyme that has little or no activity. In the ALDH-I deficient population, alcoholism and alcohol abuse virtually do not exist. The effect of daidzin's direct, potent inhibition of ALDH-I mimics the effect of this naturally-occurring ALDH-I genetic mutation. As shown by the purification scheme described in Example 1, no other inhibitors of similar selectivity and potency were discovered in the extract of RP, which contains a multiplicity of chemical components, only few of which have been previously identified. While daidzin is a known component of RP, prior to the present invention, the art has not been provided with a reason for and the identification of activity of components of RP involved in and responsible for effects on the metabolism of ethanol in humans and/or the mediation of the behavioral effects of ethanol by that means. Further RP has been used in Traditional Chinese medicine for the treatment of excess alcohol consumption and as an agent to increase ethanol elimination. Therefore, it was expected that RP would contain components that activated ALDH (and ADH) rather than components that would inhibit isozyme activity. Such activation would be expected since RP is administered by Chinese herbalists to help eliminate the consumed alcohol more quickly. Information from China indicates that administered RP increases metabolic rate and elimination, induces intense perspiration as one aspect of the increased elimination, and has the effect of accelerating the return to sobriety after acute intoxication, without the fear of use that has been associated with the administration of disulfiram or cyanamide.

As shown in Example 2, highly purified human ALDH-I and ALDH-II isozymes were obtained and used in a series of assays to determine the inhibitory activity of a variety of compounds, including some components of RP.

As shown in Example 3, numerous compounds, including other components of RP, as well as compounds structurally related to daidzin, were tested but were not found to have the direct, potent yet selective, inhibitory effect on human ALDH-I. The only other compounds tested that showed a selective inhibitory effect on ALDH-I were prunetin and genistin, however, their potency as inhibitors were approximately 10-fold less than that of daidzin. ALDH-I is thought to be the major isozyme in acetaldehyde detoxification due to its high affinity (low $K_m$) for acetaldehyde. A large proportion of the compounds examined for inhibitory effect were benzo[b]pyran derivatives and are either chromones, isoflavones or coumarins. Thus, chromone is 4-H-benzo[b]pyran-4-one; coumarin is 2H-benzo[b]pyran-2-one; flavone is 2-phenylchromone and isoflavone is 3-phenylchromone. Structures I, II and III, shown as follows with ring numbering, illustrate chromones, coumarins and isoflavones, respectively, and should be used in evaluating the data in Tables IV and V of Example 3:

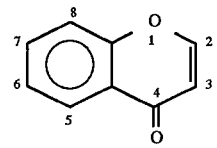

I

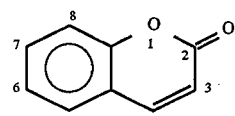

II

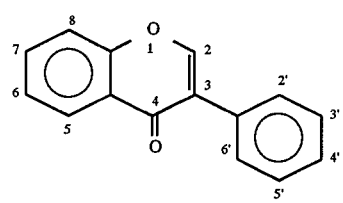

III

Examples of reduced pyran rings are included. In flavans and isoflavans, the pyran ring of the chromone moiety is fully saturated at the 2,3 and 4 positions. The numbering systems which these compounds have in common allows facile tabular comparison of substituent effects (see Tables IV and V of Example 3).

As shown in Examples 4, 5, 6, and 7, daidzin present in an RP extract or as a purified component from the extract, has significant in vivo effects on alcohol consumption. These experiments were designed to test the effect of daidzin on free choice ethanol intake in golden hamsters. Initially, an acclimation period and a pretreatment period were used to establish an ethanol/water preference ratio, as well as an overall pattern of consistent fluid intake. After the animals received daidzin in the extract or purified from the extract, the ethanol/water preference ratio decreased dramatically, indicating that daidzin was effective in what may be considered alcohol intolerance therapy. The bioavailability of daidzin administered as a crude extract is significantly increased (e.g., 5–10 fold as shown in Example 7) as compared with the bioavailability of daidzin administered as a purified (e.g., synthetic) compound. Daidzin is thus useful in a pharmaceutical composition to inhibit ALDH-I. Pharmaceutical compositions comprising an ALDH-I inhibitory compound, such as daidzin and to a lesser extent prunetin and genistin, are useful in methods for alcohol intolerance and in methods for the treatment of alcoholism or alcohol abuse.

As shown in Examples 8, 9 and 10, daidzin analogs with inhibitory properties which mimic daidzin, were synthesized and used in experiments in vitro and in vivo similar to those experiments described in Examples 3–7 using daidzin. Daidzin analogs according to the present invention were potent ALDH-I inhibitors and even if somewhat less selective for ALDH-I than daidzin, these analogs were found to have significant in vivo effects on alcohol consumption in an animal model, similar to daidzin.

An ALDH-I inhibitory compound according to the present invention may be administered orally, parenterally, by inhalation or spray or rectally in dosage unit formulations containing conventional non-toxic pharmaceutically acceptable carriers, adjuvants and vehicles. The term parenteral as used herein includes subcutaneous injections, intravenous, intramuscular, intrasternal injection or infusion techniques.

In addition, there is provided a pharmaceutical formulation comprising an ALDH-I inhibitory compound according to the present invention and a pharmaceutically acceptable carrier. An ALDH-I inhibitory compound according to the present invention may be present in association with one or more non-toxic pharmaceutically acceptable carriers and/or diluents and/or adjuvants and if desired other active ingredients. The pharmaceutical compositions containing an ALDH-I inhibitory compound according to the present invention may be in a form suitable for oral use, for example, as tablets, troches, lozenges, aqueous or oily suspensions, dispersible powders or granules, emulsion, hard or soft capsules, or syrups or elixirs. Oral administration is a highly preferred route of administration using an ALDH-I inhibitory compound according to the present invention.

In addition to the use of conventional forms of drug administration as outlined above, a number of novel drug delivery approaches have been developed as described by Langer, 1990, Science 249:1527–1533, which may be used to administer an ALDH-I inhibitory compound according to the present invention. These approaches for drug delivery include drug modification by chemical means, drug entrapment in small vesicles that are injected into the blood stream and drug entrapment within pumps or polymeric materials that are placed in desired bodily compartments, for example, beneath the skin, or transdermal delivery, for example via skin patches.

Compositions intended for oral use may be prepared according to any method known to the art for the manufacture of pharmaceutical compositions and such compositions may contain one or more agents selected from the group consisting of sweetening agents, flavoring agents, coloring agents and preserving agents in order to provide pharmaceutically elegant and palatable preparations. Tablets contain the active ingredient in admixture with non-toxic pharmaceutically acceptable excipients which are suitable for the manufacture of tablets. These excipients may be for example, inert diluents, such as calcium carbonate, sodium carbonate, lactose, calcium phosphate or sodium phosphate; granulating and disintegrating agents, for example, corn starch, or alginic acid; binding agents, for example starch, gelatin or acacia, and lubricating agents, for example magnesium stearate, stearic acid or talc. The tablets may be uncoated or they may be coated by known techniques to delay disintegration and absorption in the gastrointestinal tract and thereby provide a sustained action over a longer period. For example, a time delay material such as glyceryl monostearate or glyceryl distearate may be employed. A slow-release formulation of an ALDH-I inhibitory compound according to the present invention may enhance effectiveness of the compound.

Formulations for oral use may also be presented as hard gelatin capsules wherein the active ingredient is mixed with an inert solid diluent, for example, calcium carbonate, calcium phosphate or kaolin, or as soft gelatin capsules wherein the active ingredient is mixed with water or an oil medium, for example peanut oil, liquid paraffin or olive oil.

Aqueous suspensions contain the active material in admixture with excipients suitable for the manufacture of aqueous suspensions. Such excipients are suspending agents, for example sodium carboxymethylcellulose, methylcellulose, hydroxypropylmethylcellulose, sodium alginate, polyvinylpyrrolidone, gum tragacanth and gum acacia; dispersing or wetting agents may be a naturally-occurring phosphatide, for example, lecithin, or condensation products of an alkylene oxide with fatty acids, for example polyoxyethylene stearate, or condensation products of ethylene oxide with long chain aliphatic alcohols, for example heptadecaethyleneoxycetanol, or condensation products of ethylene oxide with partial esters derived from fatty acids and a hexitol such as polyoxyethylene sorbitol monooleate, or condensation products of ethylene oxide with partial esters derived from fatty acids and hexitol anhydrides, for example polyethylene sorbitan monooleate. The aqueous suspensions may also contain one or more preservatives, for example ethyl, or n-propyl p-hydroxybenzoate, one or more coloring agents, one or more flavoring agents, and one or more sweetening agents, such as sucrose or saccharin.

Oily suspensions may be formulated by suspending the active ingredients in a vegetable oil, for example arachis oil, olive oil, sesame oil or coconut oil, or in a mineral oil such as liquid paraffin. The oily suspensions may contain a thickening agent, for example beeswax, hard paraffin or cetyl alcohol. Sweetening agents such as those set forth above, and flavoring agents may be added to provide palatable oral preparations. These compositions may be preserved by the addition of an anti-oxidant such as ascorbic acid.

Dispersible powders and granules suitable for preparation of an aqueous suspension by the addition of water provide the active ingredient in admixture with a dispersing or wetting agent, suspending agent and one or more preservatives. Suitable dispersing or wetting agents and suspending agents are exemplified by those already mentioned above. Additional excipients, for example sweetening, flavoring and coloring agents, may also be present.

Pharmaceutical compositions of the invention may also be in the form of oil-in-water emulsions. The oily phase may be a vegetable oil, for example olive oil or arachis oil, or a mineral oil, for example liquid paraffin or mixtures of these. Suitable emulsifying agents may be naturally-occurring gums, for example gum acacia or gum tragacanth, naturally-occurring phosphatides, for example soy bean, lecithin, and esters or partial esters derived from fatty acids and hexitol, anhydrides, for example sorbitan monooleate, and condensation products of the said partial esters with ethylene oxide, for example polyoxyethylene sorbitan monooleate. The emulsions may also contain sweetening and flavoring agents.

Syrups and elixirs may be formulated with sweetening agents, for example glycerol, propylene glycol, sorbitol or sucrose. Such formulations may also contain a demulcent, a preservative and flavoring and coloring agents. The pharmaceutical compositions may be in the form of a sterile injectable aqueous or oleagincus suspension. This suspension may be formulated according to the known art using those suitable dispersing or wetting agents and suspending agents which have been mentioned above. The sterile injectable preparation may also be sterile injectable solution or suspension in a non-toxic parenterally acceptable diluent or solvent, for example as a solution in 1,3-butanediol. Among the acceptable vehicles and solvents that may be employed are water, Ringer's solution and isotonic sodium chloride solution. In addition, sterile, fixed oils are conventionally employed as a solvent or suspending medium. For this purpose any bland fixed oil may be employed including synthetic mono- or diglycerides. In addition, fatty acids such as oleic acid find use in the preparation of injectables.

An ALDH-I inhibitory compound according to the present invention may also be administered in the form of suppositories for rectal administration of the drug. These compositions can be prepared by mixing the drug with a suitable non-irritating excipient which is solid at ordinary temperatures but liquid at the rectal temperature and will therefore melt in the rectum to release the drug. Such materials are cocoa butter and polyethylene glycols.

An ALDH-I inhibitory compound according to the present invention may be administered parenterally in a sterile medium. The drug, depending on the vehicle and concentrations used, can either be suspended or dissolved in the vehicle. Advantageously, adjuvants such as local anesthetics, preservatives and buffering agents can be dissolved in the vehicle.

Finally, an ALDH-I inhibitory compound according to the present invention may be administered as an implant.

Dosage levels of the order of from about 0.1 mg to about 140 mg per kilogram of body weight per day are useful in the treatment of the above-indicated conditions (from about 1.0 mg to about 50.0 g per 70 kg patient per day). The amount of active inhibitor that may be combined with the carrier materials to produce a single dosage form will vary depending upon the host treated and the particular mode of administration. Dosage unit forms will generally contain between from about 1 mg to about 500 mg of an active ingredient.

It will be understood, however, that the specific dose level for any particular individual will depend upon a variety of factors including the activity of the ALDH-I inhibitor, the age, body weight, general physical and mental health, genetic factors, environmental influences, sex, diet, time of administration, route of administration, and rate of excretion, drug combination and the severity of the particular problem undergoing treatment or therapy. For example, the dose level useful for inducing alcohol intolerance may vary among individuals depending on the severity of their alcohol abuse problem. Similarly, the dose level for suppressing an urge for alcohol may vary among individuals, depending on the severity of the individual's alcoholism symptoms. Further, the dose level for preventing alcoholism in an individual with a susceptibility to alcoholism or alcohol abuse may vary depending on the causative factors of the susceptibility as well as the severity of the predisposition.

EXAMPLE 1

Isolation of ALDH Inhibitors

The crude drug Radix Puerariae (RP) prepared as the dried root of *Pueraria lobata* was purchased from a local herbal medicine store, Vinh-Kan Ginseng Co., Boston, Mass. The crude drug was prepared and packaged by South Project Chinese Herbs Factory, Shenzhen, Kwang Tong, The People's Republic of China and was distributed by South Project Ltd., 37 Ko Shing St., Block C, 2/F, Hong Kong. RP may also be purchased from other herbal medicine stores, for example, the Lee-Yuen-Cheong Herbal Medicine Store in Hong Kong.

An ALDH inhibitor, later identified as the isoflavone daidzin, was isolated from a methanol extract of RP by chromatography on BioGel P-4 and reverse phase HPLC columns. Specifically, daidzin was isolated from RP according to the following scheme:

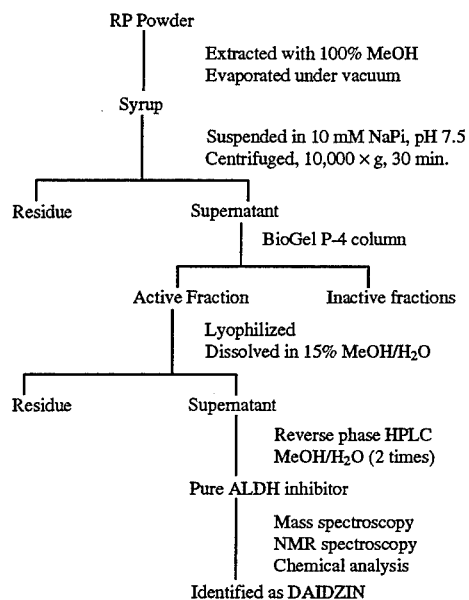

Figure 2:
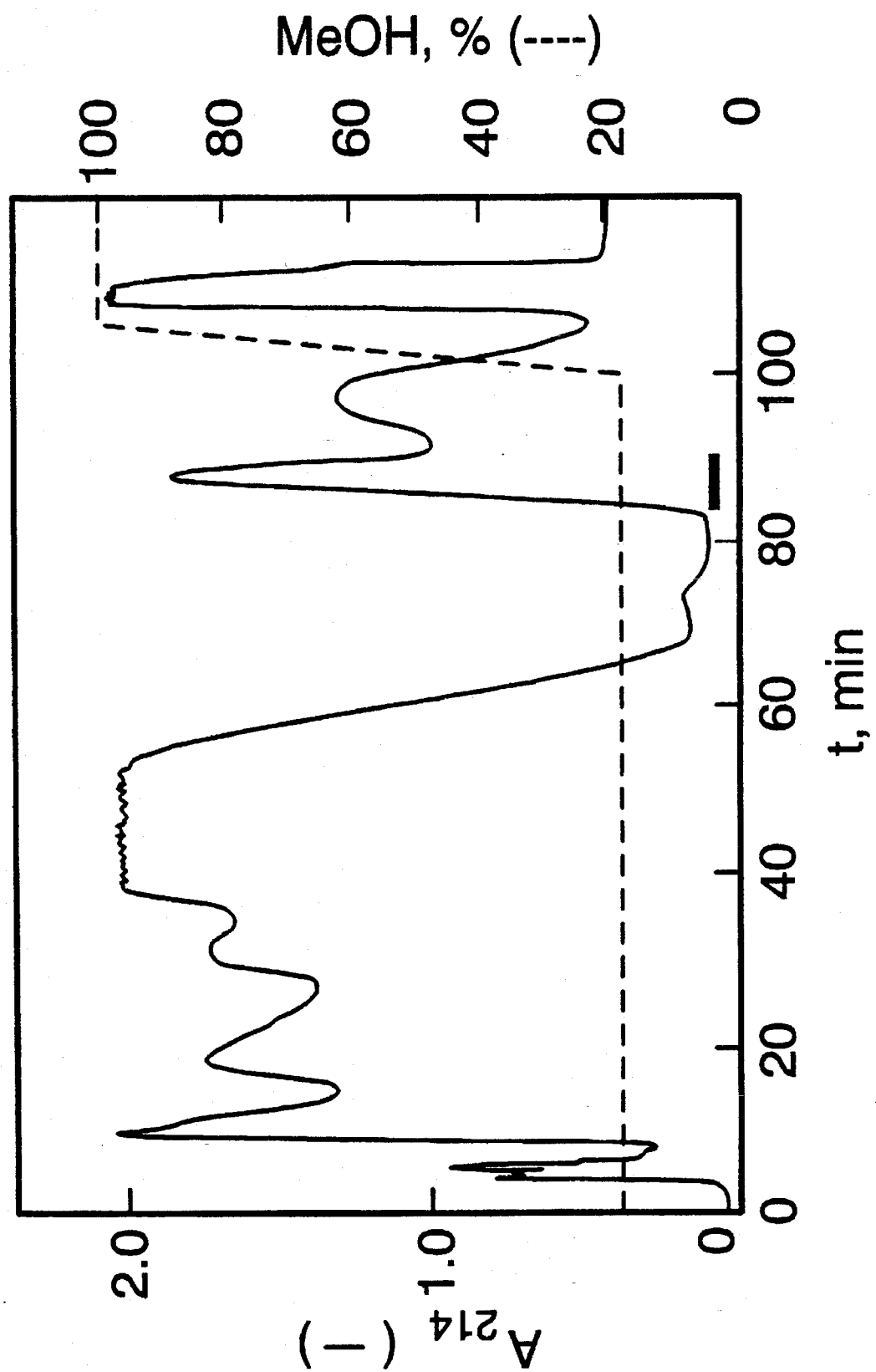
FIG. 2 is a HPLC chromatogram of an ALDH inhibitor partially purified on a BioGel P-4 column (FIG. 1). Fractions containing ALDH inhibitory material, indicated by the horizontal bar, were pooled and dried.
Figure 3:
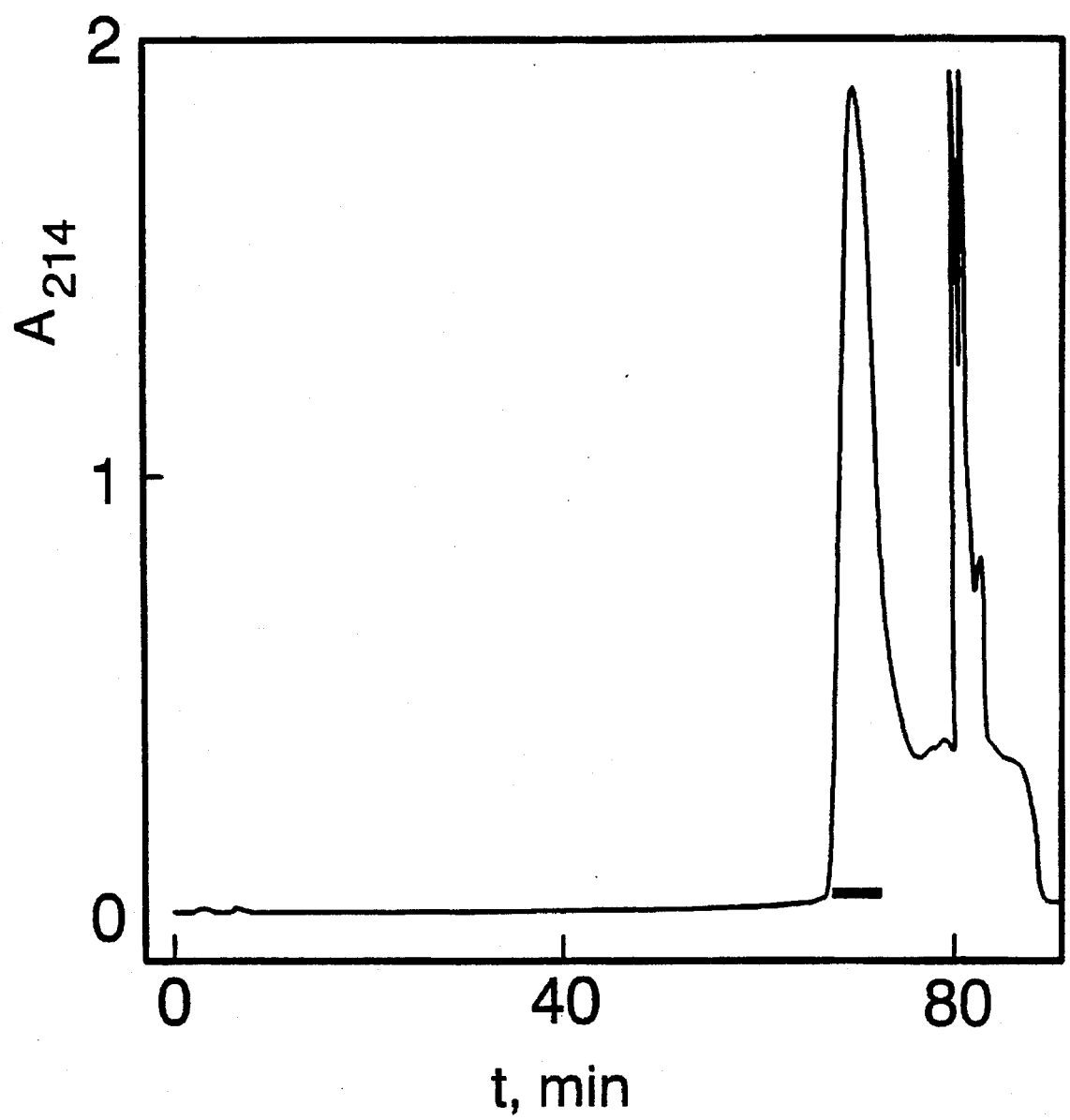
FIG. 3 is a graph of a HPLC elution profile of the ALDH inhibitory material obtained in FIG. 2.

In the first step of the above scheme, dried RP, 10 g, was ground to a powder in a domestic food processor and extracted with 100 ml of methanol for 10 hours in a Soxhlet extractor equipped with an all-glass extraction thimble (Kontes, Vineland, N.J.). In the next step, methanol was removed from the extract by vacuum evaporation and the resultant syrup was dissolved in 5 ml of 10 mM sodium phosphate, pH 7.5. In the following step, undissolved materials were removed by centrifugation in a Sorvall RC5B superspeed centrifuge (10,000 rpm, 30 minutes) with a SS-34 rotor (DuPont, Wilmington, Del.). Then, the supernatant solution was applied to a BioGel P-4 (BioRad Laboratories, Richmond, Calif.) column (3.5×55 cm) equilibrated with the same buffer. The column was eluted at 55 ml/hour and fractions of 11 ml were collected. A representative elution diagram as measured by absorbance at 214 nm is shown in FIG. 1 (solid circles). Those fractions, shown in FIG. 1 as open circles, that exhibited ALDH inhibitory activity (assayed as described below) were pooled, lyophilized and redissolved in 15% methanol in water. Next, the solution was filtered (Millipore Millex filter, 0.45µ) and injected onto a HPLC column (Waters, Milford, Mass.; NovaPak, C18 column, 6–8µ, 7.8 mm×30 cm). The column was eluted at 2 ml/minute with 15% methanol/water. A representative elution pattern is shown in FIG. 2; absorbance at 214 nm over time in minutes is shown as a solid line, while percent methanol in the gradient over time in minutes is shown as a broken line. The ALDH inhibitor eluted at about 87 minutes (FIG. 2). This inhibitory material was rechromatographed on the same column pre-equilibrated with and eluted with 20% methanol/water to yield a single highly purified substance as shown in FIG. 3. A further rechromatography under the latter conditions yielded the ALDH inhibitor daidzin as identified by four methods: (i) mass spectroscopy; (ii) NMR spectroscopy; (iii) chemical analysis; and (iv) cochromatography with an authentic sample of daidzin (Indofine Chemical Co., Somerville, N.J.).

Mass spectroscopy was performed using a Hewlett Packard 5985B GC/MS at 70 eV in an electron ionization mode. The sample of ALDH inhibitor was introduced with a direct insertion probe and the temperature of the probe was raised from room temperature to 295° C. The resultant mass spectrum of the ALDH inhibitor shows fragment ion peaks at m/z 118, 136 and an apparent molecular ion peak at m/z 254. This spectrum is identical to that of the authentic compound daidzein (Ganguly and Sarre, 7 Feb. 1970, Chemistry and Industry, p. 201). Since daidzein has a melting point of 300° C. (Ganguly and Sarre, 1970, supra) and it does not inhibit ALDH (Table V), the isolated ALDH inhibitor is a derivative of daidzein with chemical group(s) labile to the conditions under which the mass spectrum was obtained.

$^1$H NMR spectra were acquired at 25° C. in deuterated dimethylsulfoxide, $d_6$-DMSO, (Sigma Chemical Co., St. Louis, Mo.) using a 30 degree excitation pulse in a Varian VXR 300S NMR spectrometer operating at 299.949 Megahertz. The $^1$H NMR spectrum obtained for the authentic daidzein is consistent with that reported previously (Kitada et al., 1985, J. Chromatography 347:438–442). A tentative assignment of all the $^1$H NMR signals in the NMR spectrum was made based on reference spectra in Mabry et al., 1970, In: *The Systematic Identification of Flavonoids* (Mabry et al., eds.), Chapter VIII, Springer-Verlag, N.Y. The reported spectrum was identical with that of an authentic sample of daidzein [ε 10.78, 7OH; 9.515, 4'OH; 8.28, H2; 7.953 (d,J=8.79), H5; 7.37 (d,J=8.30), H2' and H6'; 6.925 (q,J=2.2, 8.55), H6; 6.851 (d,J=2.2), H8; 6.795 (d,J=8.30), H3' and H5']. The $^1$H NMR spectrum of the ALDH inhibitor was acquired under the same conditions [ε 9.54, 4'OH; 8.38, H2; 8.036 (d,J=8.79), H5; 7.396 (d,J=8.79), H2' and H6'; 7.222 (d,J=1.95), H8; 7.13 (q,J=2.44,8.79), H6; 6.804 (d,J=8.79), H3' and H5'; multiplets at 5.43 (1H), 5.0–5.2 (3H) and 4.6 (1H)]. In the low field region, signals for all but the 7-OH protons on daidzein were also observed for the ALDH inhibitor. The lack of the 7-OH signal was probably not due to a rapid exchange with $D_2O$ because the 4'-OH proton which is also water-exchangeable gave rise to a strong and sharp transition at 9.54 ppm. The fact that additional signals were observed in the high field region for the ALDH inhibitor suggested that the inhibitor is a substituted daidzein. The lack of 7-OH signal suggests the substituent is attached to the 7-position of the daidzein aglycone. Based on the facts that the ALDH inhibitor has a melting point (see Merck Index) and NMR spectrum (see Kitada et al., 1985, supra) similar to that reported for daidzin, the ALDH inhibitor isolated from RP is therefore daidzin, the 7-glucoside of daidzein.

To demonstrate that the ALDH inhibitor isolated from RP was daidzin, a 7-glucoside of daidzein, the sample was hydrolyzed in 2N HCl for 15 hours at 70° C., a condition under which glycosidic linkages are cleaved (Beeley, 1985, In: *Laboratory Techniques in Biochemistry and Molecular Biology—Glycoprotein and Proteoglycan Techniques*, (Burdon and van Knippenberg, eds.), pp. 100–152, Elsevier Science Publishers B. V., Amsterdam). Hydrolyzed samples were spotted onto three Silica Gel 60 F-254 precoated TLC plates, layer thickness 0.2 mm (E. Merck, Darmstadt, Germany) and the plates were developed in three different solvent systems: (I) ethylmethyl ketone:glacial acetic acid:methanol (6:2:2) (Stahl and Kaltenbach, 1965, In: *Thin-Layer Chromatography—A Laboratory Handbook*, (Stahl, ed.), pp. 461–469, Springer-Verlag, A/P N.Y.), (II) benzene:glacial acetic acid: methanol (2:2:6) (Stahl and Kaltenbach, 1965, supra) and (III) formic acid:chloroform:acetone (8.5:75:16.5) (Wagner et al., 1984, In: *Plant Drug Analysis*, (Scott, trans.), pp. 163–193, Springer-Verlag, Berlin, Heidelberg). Authentic D-glucose and daidzein were also spotted onto the TLC plates as standards. Unhydrolyzed ALDH inhibitor was run as a control. Daidzein and ALDH inhibitor on the TLC plates were visualized by fluorescence quenching under short wavelength (254 nm) UV light; glucose and ALDH inhibitor were visualized by anisaldehyde (Sigma Chemical Co., St. Louis, Mo.) spray (Stahl and Kaltenbach, 1961, J. Chromatography 5:351–355). The fact that ALDH inhibitor can be visualized also by the anisaldehyde reagent suggested that the inhibitor contained not only a daidzein moiety as suggested by mass spectral data but also a carbohydrate component.

The $R_f$ values of daidzin, daidzein, glucose, ALDH inhibitor and acid hydrolyzed ALDH inhibitor obtained in different solvent systems are given in Table I.

TABLE I $R_f \times 100$ values of glucose, daidzein, unhydrolyzed and acid hydrolyzed ALDH inhibitor

|  | Solvent System | | |
|---|---|---|---|
|  | I | II | III |
| Glucose | 40$^a$ | 73$^a$ | — |
| Daidzein | 85$^b$ | 96$^b$ | 43$^b$ |
| ALDH Inhibitor | 69$^{a,b}$ | 91$^{a,b}$ | 2$^{a,b}$ |
| Acid hydrolyzed ALDH Inhibitor | 40$^a$ | 73$^a$ | — |
| Acid hydrolyzed ALDH Inhibitor | 85$^b$ | 96$^b$ | 43$^b$ |
| Daidzin | 69$^{a,b}$ | 91$^{a,b}$ | 2$^{a,b}$ |

$^a$Detected by anisaldehyde reagent
$^b$Detected under UV.

The unhydrolyzed ALDH inhibitor ran as a single spot with $R_f$ values between those of glucose and daidzein and comigrated with an authentic sample of daidzin. Upon hydrolysis, ALDH inhibitor was cleaved into two components. One component was detected under UV and had $R_f$ values identical to those of daidzein in all three solvent systems studied. The other component was detected by anisaldehyde reagent and had $R_f$ values identical to those of glucose in solvent system I and II. The TLC run in solvent system III was not developed with anisaldehyde reagent because of high background. These results, together with results from melting point analysis, mass and nuclear magnetic resonance spectroscopy analysis demonstrated that the ALDH inhibitor isolated from RP was daidzin, a 7-glucoside of daidzein.

To monitor the purification of the ALDH inhibitor, fractions were assayed for ALDH inhibitory activity. To determine whether a fraction contained ALDH inhibitory activity, ALDH activities were measured in the presence and absence of 50 μl of each fraction in our standard pH 9.5 ALDH assay medium (Fong et al., 1989, supra) 0.1M in glycine-NaOH, 0.15M in KCl, 0.6 mM in NAD$^+$ (Grade III, Sigma Chemical Co., St. Louis, Mo.), 30 μM in acetaldehyde and preferably 5–10 nM in ALDH-I (purified according to Example 2) or a mixture of ALDH-I and ALDH-II (obtained after the AMP-agarose column step described in Example 2). The enzyme reaction rates were measured by monitoring the production of NADH at 340 nm (ε=6.22 mM$^{-1}$ cm$^{-1}$) with a Varian Cary 219 spectrophotometer thermostated at 25° C. ALDH inhibition was calculated by the following equation:

$$\% \text{ inhibition} = \frac{V_o - V_i}{V_o} \times 100$$

where $V_o$ is the enzyme reaction rate measured in the absence of the sample fraction and where $V_i$ is the enzyme reaction rate measured in the presence of the 50 μl sample fraction.

EXAMPLE 2

Purification of ALDH isozymes

Human livers were obtained at autopsy within 12 hours postmortem and were stored at −70° C. A modification of the procedure of Ikawa et al., 1983, J. Biol. Chem. 258:6282–6287, was used to purify ALDH-I and ALDH-II isozymes. A Caucasian liver sample (50 g wet weight) with the usual Caucasian ALDH phenotype (both ALDH-I and ALDH-II present) was homogenized at 0° C. in 100 ml pH 6.0 buffer 15 mM in sodium phosphate, 0.5 mM in EDTA, 0.5 mM in dithiothreitol (DTT; Sigma Chemical Co., St. Louis, Mo.). The homogenate was centrifuged at 4° C. in a Beckman (Beckman Instruments Inc., Irvine, Calif.) L8-M ultracentrifuge at 92,000×g for 90 minutes. The clear supernatant solution was diluted to a final volume of 200 ml with cold water and loaded at ambient temperature onto a carboxymethyl cellulose cake (CM-52, Whatman Lab Sales, Clifton, N.J.) packed in a 9.5×4 cm sintered glass funnel and equilibrated with homogenizing buffer. Both ALDH-I and ALDH-II eluted in the void volume of the CM-52 cake and this fraction was immediately loaded onto a 1.5×20 cm AMP-Agarose (A-3019, Sigma Chemical Co., St. Louis, Mo.) column equilibrated with 2× homogenizing buffer in the cold room. The AMP-column was first washed with 100 ml of column buffer and then eluted with a 400 ml linear gradient of 0–5 mM $NAD^+$ in column buffer. Fractions containing ALDH activity (assayed as described in Example 1) were pooled, concentrated to about 8 ml with an Amicon PM-30 membrane (Amicon Division, W. R. Grace & Co., Danvers, Mass.) and dialyzed in the cold room overnight against 4 liters of pH 8.0 buffer 10 mM in Tris-HCl and 1 mM in DTT for further purification on HPLC.

The HPLC fractionation of ALDH isozymes was performed with a Waters gradient chromatographic system (Waters, Milford, Mass.) consisting of two M45 pumps, U6K injector equipped with a 2 or 10 ml injection loop, Model 482 variable wavelength UV/VIS detector, model 680 automated gradient controller, and 740 data module. Fractionation of less than 10 mg total protein was carried out at room temperature on an analytical Protein-Pak DEAE 5PW anion exchange HPLC column (0.75×7.5 cm) (Waters, Milford, Mass.) at a flow rate of 1 ml/minute. For protein loads of greater than 10 mg fractionation was carried out on a semi-preparative scale version of the same column (2.15× 15 cm) at 5 ml/minute. As much as 150 mg protein could be loaded onto the semi-preparative column without an overloading problem. The dialyzed ALDH samples were filtered and were loaded (1–10 ml) onto a column previously equilibrated with dialysis buffer. Elution was effected with NaCl gradients in equilibration buffer as detailed below.

Figure 4:
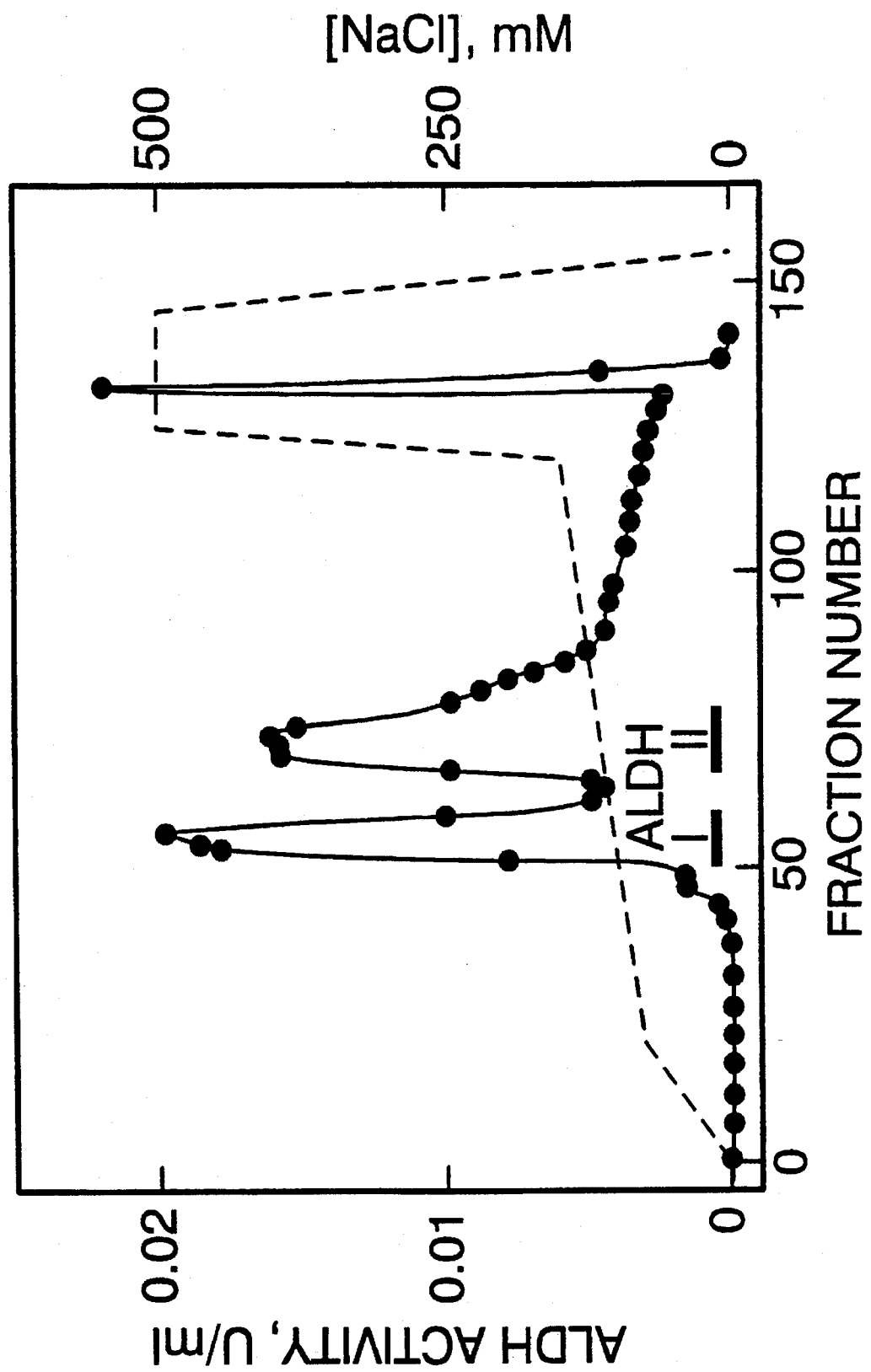
FIG. 4 is a graph of a HPLC elution profile of human ALDH activity eluted from an AMP-agarose column. Fractions containing ALDH-I and ALDH-II activities were pooled and concentrated.
Figure 5:
FIG. 5 is a picture of a starch gel electrophoretogram of ALDH-I and ALDH-II preparations shown in FIG. 4.
Figure 5:
Figure 6:
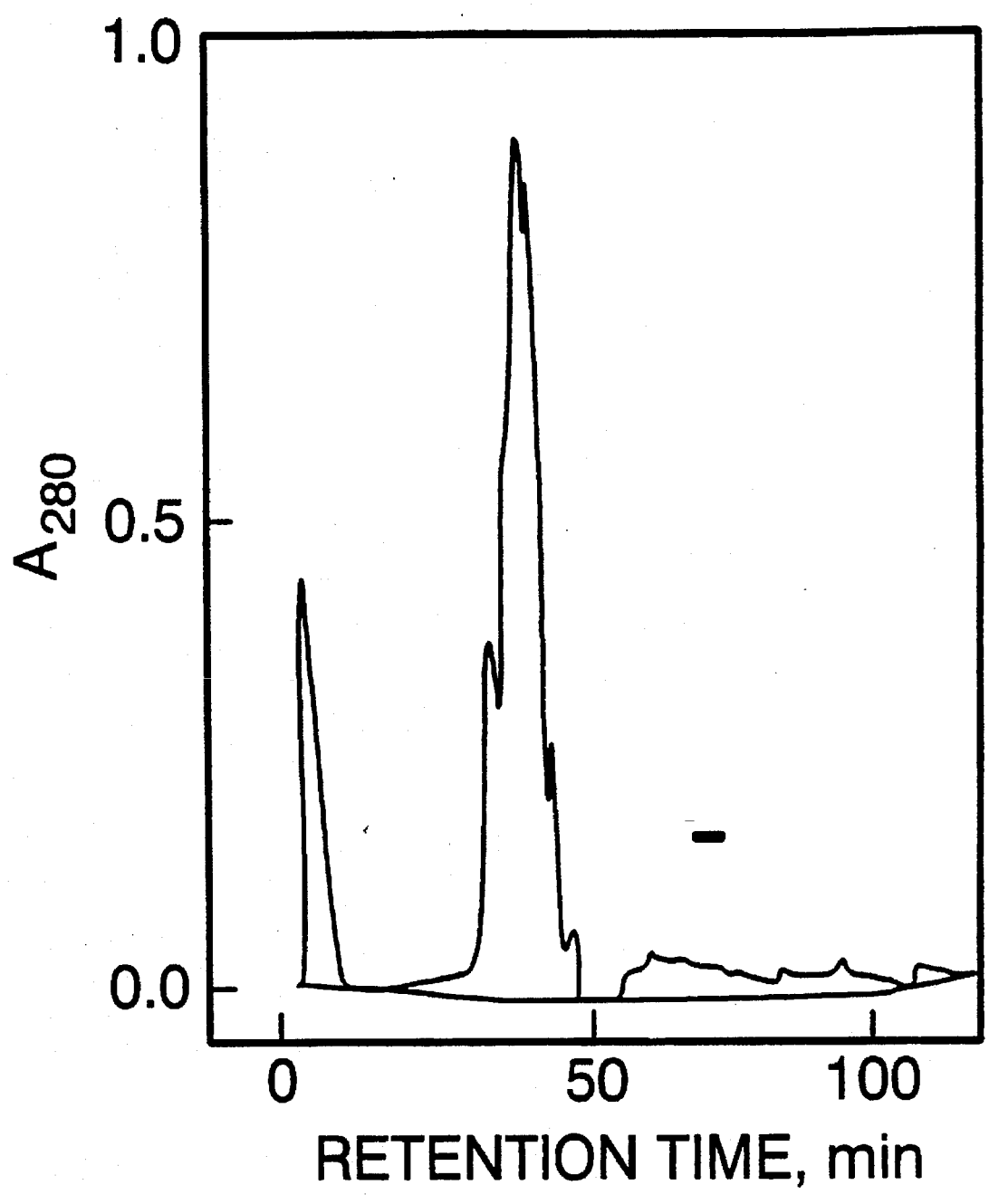
FIG. 6 is the HPLC chromatogram of the semi-purified ALDH-I of FIG. 4. Fractions containing ALDH-I activity, indicated by the horizontal bar, were pooled and concentrated.
Figure 7:
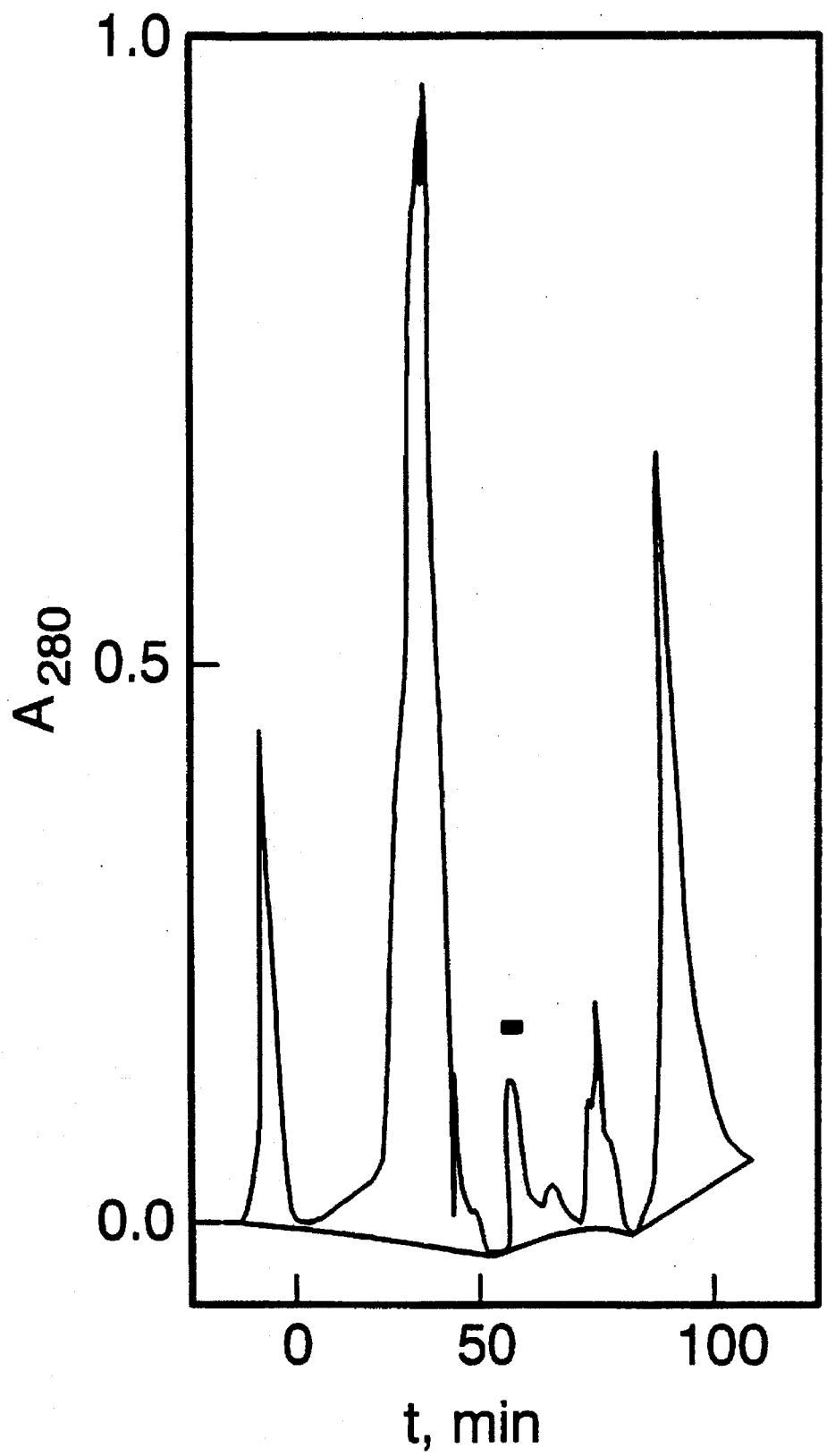
FIG. 7 is the HPLC chromatogram of the semi-purified ALDH-II of FIG. 4. Fractions containing ALDH-II activity, indicated by the horizontal bar, were pooled and concentrated.

The AMP-Agarose column eluate (~100 mg total protein) was first loaded onto a semi-preparative DEAE 5PW HPLC column and the ALDH-I and ALDH-II were resolved, as shown in FIG. 4, with the following NaCl gradient: 0–20 minute, 0–75 mM, linear; 20–120 minute, 75–100 mM, linear; 120–125 minute, 100–500 mM, linear; 125–145 minute, 500 mM, isocratic; 145–155 minute, 500–0 mM, linear. A representative HPLC chromatograph of the ALDH isozymes from the AMP-agarose column is shown in FIG. 4; the solid line shows ALDH activity in units/ml and the broken line shows the NaCl (mM) gradient as plotted against fraction number. At this stage, ALDH-I and ALDH-II isozymes were well resolved as shown in FIG. 5 by starch gel electrophoresis according to the method of Harada et al., 1980, Am. J. Hum. Genet. 32:8–15, but were still heavily contaminated by non-ALDH proteins. The individual ALDH isozymes were pooled and dialyzed against the same buffer and were rechromatographed on an analytical DEAE 5PW HPLC column. For ALDH-I, elution was affected with the following NaCl gradient: 0–160 minute, 0–500 mM, linear; 160–190 minute, 500 mM, isocratic; 190–195 minute, 500–0 mM, linear. The results of a representative elution profile in the isolation of ALDH-I is shown in FIG. 6. For ALDH-II, a shallower NaCl gradient was used: 0–80 minute, 0–200 mM, linear; 80–100 minute, 200–500 mM, linear; 100–130 minute, 500 mM, isocratic; 130–135 minute, 500–0 mM, linear. The results of a representative elution profile in the isolation of ALDH-II is shown in FIG. 7. The ALDH isozymes after second HPLC were about 95–98% pure as judged by SDS gel electrophoresis (Laemmli and Favre, 1973, J. Mol. Biol. 80:575–599) and were used for kinetic analysis as described in Example 3.

EXAMPLE 3

Inhibition of ALDH by Daidzin and Related Compounds

Although daidzin is a known major constituent of *Pueraria lobata* (Nakamoto et al., 1977, supra; Chén and Zhang, 1985, supra) and other plants (Eldridge and Kwolak, 1983, J. Agric. Food & Chem. 31:394–396), its effects on human alcohol metabolism were unknown. In particular, its ability to inhibit ALDH has not previously been reported or suggested.

The kinetic properties of daidzin toward human ALDH-I and ALDH-II were studied using formaldehyde as substrate. The most commonly used substrate, acetaldehyde, has an extremely low $K_m$ value (~2 μM) for ALDH-I which does not permit accurate analysis of its kinetics by the spectrophotometric method. The $K_m$ values of formaldehyde for ALDH-I and ALDH-II, as determined in the present study, were 800 μM and 6.6 mM, respectively. These values are within the same range to those reported for the horse mitochondrial and cytosolic ALDH isozymes respectively (Pietruszko, 1989, supra).

The inhibition kinetics were studied by the initial velocity method (Dixon and Webb, 1979, Enzymes, 3rd ed., Longman, Great Britain). Daidzin was dissolved at different concentrations in methanol and was added to the assay medium as 10 μL aliquots. For controls, 10 μL of methanol was added to the assay medium. The initial reaction rates were measured in a pH 9.5 assay medium 0.1M in glycine-NaOH, 0.15M in KCl, 1 mM in $NAD^+$, 1% in methanol, 10 nM in ALDH-I or ALDH-II and various concentrations of formaldehyde and daidzin. The enzyme reaction rates were followed by monitoring the production of NADH at 340 nm ($\epsilon=6.22$ $mM^{-1}cm^{-1}$) with a Varian Cary 219 spectrophotometer thermostated at 25° C. The kinetic data were analyzed by standard graphical methods. Type of inhibition and Michaelis constants for formaldehyde were analyzed by Lineweaver-Burk plots and the inhibition constants were estimated by Dixon plots (Dixon and Webb, 1979, supra). The kinetic parameters are summarized in Table II.

TABLE II

Kinetic Constants for Daidzin Inhibition of
Human ALDH-I and ALDH-II Isozymes

| Isozyme | $K_i$ (nM) |
| --- | --- |
| ALDH-I | 40 |
| ALDH-II | 20,000 |

Daidzin selectively inhibits ALDH-I at nanomolar concentrations. The data shows a 500-fold more effective inhibition of human ALDH-I than of human ALDH-II by daidzin.

Inhibition of ALDH-I by daidzin is reversible. Preincubation of ALDH-I with 100 nM daidzin results in 70% inhibition which is reversed by 100-fold dilution to yield a final inhibition of 2%. These facts point to daidzin as a safe, effective and reversible means to achieve alcohol intolerance along the lines naturally available to ALDH-I deficient Oriental individuals.

By the same token, genistin (Table III) is also a safe, effective and reversible selective inhibitor of ALDH-I, although nearly an order of magnitude less potent than daidzin.

TABLE III

Kinetic Constants for Prunetin and Genistin Inhibition of Human ALDH-I and ALDH-II Isozymes

| Isozyme | $K_i$ (nM) | |
| --- | --- | --- |
|  | Prunetin | Genistin |
| ALDH-I | 300 | 360 |
| ALDH-II | 12,000 | * |

*No inhibition was observed up to 20 μM.

A survey of the inhibitory properties of commercially available compounds that are structurally similar to daidzin revealed only a few that inhibit ALDH-I as shown in Table IV, including an isoflavone, 3 flavones, a chromone, a coumarin, a dihydrocoumarin and a hexahydrocoumarin, but none as potent as daidzin. None of these are known components of RP as is daidzin. Moreover, none of these ALDH inhibitory compounds are potent yet highly selective inhibitors of ALDH-I as is daidzin, rather they show pronounced inhibition of ALDH-II.

compounds of Table V, are not inhibitory. Also 2-phenylquinoline a steric analog of isoflavone did not inhibit.

For the study of the inhibition of ALDH-I by structurally related compounds to generate the data shown in Tables IV and V, each individual compound was dissolved at different concentrations in methanol and was added to the assay medium as 10 μL aliquots. For controls, 10 μL of methanol was added to the assay medium. In a standard ALDH-I assay, the assay medium contains 0.1M sodium pyrophosphate pH 9.5, 0.15M KCl, 1 mM NAD⁺, 1% methanol, 5 μM acetaldehyde, 5–10 nM ALDH-I and various concentrations of inhibitor. The enzyme reaction rates were measured by monitoring the production of NADH at 340 nm ($\epsilon$=6.22 mM$^{-1}$ cm$^{-1}$) with a Varian Cary 219 spectrophotometer thermostated at 25° C. (Fong et al., 1989, supra). The inhibition of ALDH-I by the inhibitors was calculated as:

$$\% \text{ inhibition} = \frac{V_o - V_i}{V_o} \times 100$$

where $V_o$ is the enzyme reaction rate measured in the absence of inhibitor, and where $V_i$ is the enzyme reaction rate measured in the presence of inhibitor. The inhibitor concentration that produces 50% inhibition is defined as IC$_{50}$, a parameter that is useful for comparison of inhibition of structurally related compounds as shown in Tables IV and V. The same procedure was used for measurement of ALDH-II as for ALDH-I, except that 200 μM acetaldehyde was used in the assay medium instead of 5 μM. IC$_{50}$ values are related to the underlying $K_i$ values. For competitive inhibitors at constant initial concentration or substrate, [S$_o$], for example, daidzin, prunetin, genistin, and likely their analogs, the relevant formula is:

TABLE IV

Structurally Related Compounds That Inhibit ALDH

| Type | Substituents | | | | | | | | IC$_{50}$ (μM) | |
| --- | --- | --- | --- | --- | --- | --- | --- | --- | --- | --- |
|  | 2 | 3 | 4 | 5 | 7 | 8 | 4' | Name | ALDH-I | ALDH-II |
| Isoflavone | H |  | =O | H | OGlc | H | OH | Daidzin | 0.15 | 20 |
|  | H |  | =O | OH | OMe | H | OH | Prunetin | 1 | 12 |
|  | H |  | =O | OH | OGlc | H | OH | Genistin | 2 | # |
|  | H |  | =O | H | H | H | i-Pr | 4'-Isopropylisoflavone | 5 | 1.5 |
|  | H |  | =O | H | OGlc | H | OMe | Ononin | † | 20 |
| Flavone |  | H | =O | H | H | H | H | Flavone | 10 | 5 |
|  |  | Ph | =O | H | OH | H | H | 3-Phenyl-7-hydroxyflavone | 10 | 2 |
|  |  | H | =O | OH | OH | H | OMe | Acacetin | 5 | 5 |
| Chromone | Me | Bz | =O | H | OAc | OAc |  | 3-Benzyl-7,8-diacetoxy-2-methylchromone | 10 | 3 |
| Coumarin | =O | H | Ph | H | OH | H |  | 7-Hydroxy-4-phenylcoumarin | 10 | 0.3 |
| Dihydrocoumarin | =O | H | Ph | H | Me | H |  | 7-Methyl-4-phenyl-3,4-dihydrocoumarin | 10 | 0.5 |
| Hexahydrocoumarin | =O | Ph | Me | H | Cl | H |  | 7-Chloro-4A,5,6,7,8,8A-hexahydro-4-methyl-3-phenylcoumarin | 1 | 1 |

*ALDH activities were assayed at 25° C. in 0.1M sodium pyrophosphate buffer pH 9.5 containins 0.15M KCl, 1 mM NAD⁺, various concentrations of inhibitors and 5 and 200 μM acetaldehyde for ALDH-I and ALDH-II, respectively.
Does not inhibit ALDH-II at up to 20 μM. †IC$_{50}$ is greater than 20 μM.

Most of the flavones and isoflavones tested for ALDH inhibitory activity did not inhibit ALDH-I or ALDH-II as shown in Table V. Some of these are known components of RP and other related compounds as indicated in Table V. In addition, allantoin, a component of RP, and 1-methylhydantoin, a structural analog of 5-methylhydantoin, which are not structurally related to the $$IC_{50} = ((3[S_o]/K_m) - 1)K_i.$$

In Table IV, [S$_o$] is approximately equal to 2.5 times $K_m$ for ALDH-I and therefore IC$_{50}$ equals 6.5 times $K_i$; similarly [S$_o$] equals $K_m$ for ALDH-II measurements and IC$_{50}$ equals 2 times $K_i$.

TABLE V

Structurally Related Compounds That Do Not Inhibit ALDH†

| Type | \_ | \_ | \_ | \_ | Substituents | \_ | \_ | \_ | \_ | \_ | \_ | Name |
|---|---|---|---|---|---|---|---|---|---|---|---|---|
| | 2 | 3 | 4 | 5 | 6 | 7 | 8 | 2' | 3' | 4' | 5' | |
| Isoflavone | H | | =O | H | H | OH | H | H | H | OH | H | Daidzein* |
| | H | | =O | H | H | OH | H | H | H | OMe | H | Formononetin* |
| | H | | =O | OH | H | OH | H | H | H | OH | H | Genistein* |
| | H | | =O | OH | H | OH | H | H | H | OMe | H | Biochanin A* |
| | H | | =O | H | H | OH | OGlc | H | H | OH | H | Puerarin* |
| | Me | | =O | H | H | OAc | H | H | H | H | H | 7-Acetoxy-2-methylisoflavone |
| | Me | | =O | H | H | OAc | OAc | H | H | H | H | 7,8-Diacetoxy-2-methylisoflavone |
| Isoflavan | H | | H | H | H | OH | H | H | H | OH | H | Equol |
| Flavone | | H | =O | H | H | H | H | Cl | H | H | H | 2'-Chloroflavone |
| | | H | =O | H | H | OH | H | H | H | H | H | 7-Hydroxyflavone |
| | | H | =O | H | H | O$_2$CPh | H | H | H | H | H | 7-Benzoyloxyflavone |
| | | H | =O | H | H | OH | OH | H | H | H | H | 7,8-Dihydroxyflavone |
| | | H | =O | OH | H | OH | H | H | H | H | H | Chrysin |
| | | H | =O | OH | H | OMe | H | H | H | H | H | Techtochrysin |
| | | H | =O | OH | H | OH | H | H | H | OH | H | Apigenin |
| | | OH | =O | H | H | H | H | H | H | H | H | 3-Hydroxyflavone |
| | | OH | =O | OH | H | OH | H | H | H | H | H | Galangin |
| | | OH | =O | OH | H | OH | H | H | H | OH | H | Kaempferol |
| | | OH | =O | H | H | OH | H | H | OH | OH | H | Fisetin |
| | | OH | =O | OH | H | OH | H | OH | H | OH | H | Morin |
| | | OH | =O | OH | H | OH | H | H | OH | OH | H | Quercitin |
| | | O-rutinose | =O | OH | H | OH | H | H | OH | OH | H | Rutin |
| | | OH | =O | OH | H | OH | H | H | OH | OH | OH | Myricetin |
| Flavan | | H | =O | H | H | H | H | H | H | H | H | Flavanone |
| | | H | =O | OH | H | OH | H | H | H | OH | H | 4',5,7-Trihydroxyflavanone |
| | | OH | H | OH | H | OH | H | H | OH | OH | H | (+/−)-Catechin |
| | | OH | H | OH | H | OH | H | H | OH | OH | H | (−)-Epicatechin |
| Coumarin | =O | # | | OH | H | H | H | H | | | | Warfarin |
| | =O | H | | H | H | OMe | OMe | H | | | | 6,7-Dimethoxycoumarin* |

*Present in Radix Puerariae. #2-Acetyl-1-phenylethyl. †No inhibition observed at 20 μM inhibitor.

EXAMPLE 4

In Vivo Effects of Daidzin on Alcohol Consumption

In order to demonstrate the in vivo effect of daidzin on alcohol consumption, experiments were designed to test the effect of RP extract on free choice ethanol intake in golden hamsters. Hamsters were chosen based on previous reports that they are receptive to and give preference to high ethanol intake when compared with several other mammalian species. Hamsters drink significant quantities of ethanol in concentrations up to 70% (w/v) under free choice conditions, and drink virtually all of their daily water as ethanol at concentrations below 15%. Daily dosages of ethanol during free-choice consumption by hamsters ranges from 10 to 16 g/kg/day, equivalent to a daily consumption of 6.5 ml to 10.4 ml of 20% ethanol for a 130 g hamster (Kulkosky and Cornell, 1979, Pharmacol. Biochem. & Behav. 11:439–44). There is an inverse correlation of ethanol concentration with volume of ethanol solution consumed (Kulkosky and Cornell, 1979, supra) such that 20–30% ethanol is an appropriate concentration range over which to obtain accurate volume readings in free choice experiments.

The animals used for the experiments described in this example were six male adult golden hamsters (outbred, Lakeview Lak: LVG[SYR]), purchased from Charles River Laboratories, Wilmington, Mass. 01887. Animals were maintained on a 12/12 light/dark cycle (light on 0600–1800 hr) for a period of 6 weeks. Animals had access to food and water ad libitum.

An RP extract was prepared as follows: Dried RP, 100 g, was ground to a powder in a domestic food processor and was refluxed with 1 liter of methanol overnight in a 2 liter round bottom flask equipped with a reflux condenser, as described in Example 1. The methanol extract was passed through Whatman No. 1 filter paper to remove debris, methanol was removed from the extract by vacuum evaporation and the resultant syrup (~16 g) was suspended in 16 ml of water.

For the experiment, 6 animals were maintained as described above on a single large cage with four 250 ml calibrated drinking bottles. The drinking bottles were fitted with stainless steel straight sipper tubes, used to measure fluid consumption to the nearest 5 ml. Spillage from the drinking tubes was caught by 2 oz. jars fitted with glass funnels and positioned under the sipper tubes. Fluid consumption by the 6 hamsters was measured once every 3 days so that the consumption volumes were large enough to obtain reasonably accurate measurements.

Figure 8A:
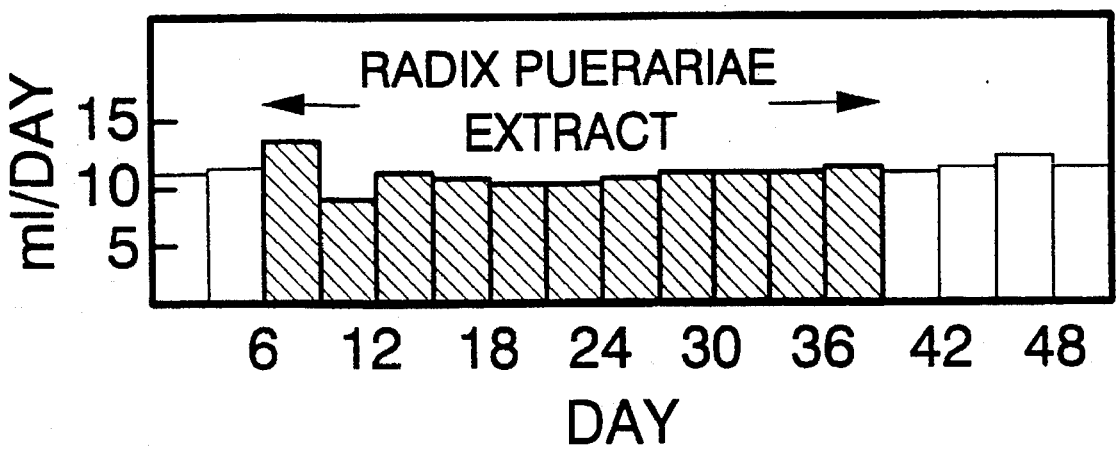
FIG. 8(A) is a histogram showing the effect of Radix Puerariae (RP) extract on the total fluid intake by golden hamsters.

After a 6-week acclimation period, the body weights of the animals reached ~180 g and stayed generally unchanged throughout the experiment. Total water intake of the animals was also stabilized at about 12 ml/day/animal as shown in FIG. 8a. Water in 2 of the 4 drinking bottles was then replaced by a 15% ethanol solution and consumption of water and aqueous ethanol were measured for a period of 2 weeks. Within 2 to 3 days after the beginning of this free choice phase of feeding, the hamsters had established an explicit preference for aqueous ethanol over water with a preference ratio (defined as aqueous ethanol intake divided by water intake) of about 8 to 9, which stayed fairly constant throughout the next 2 weeks.

Figure 8B:
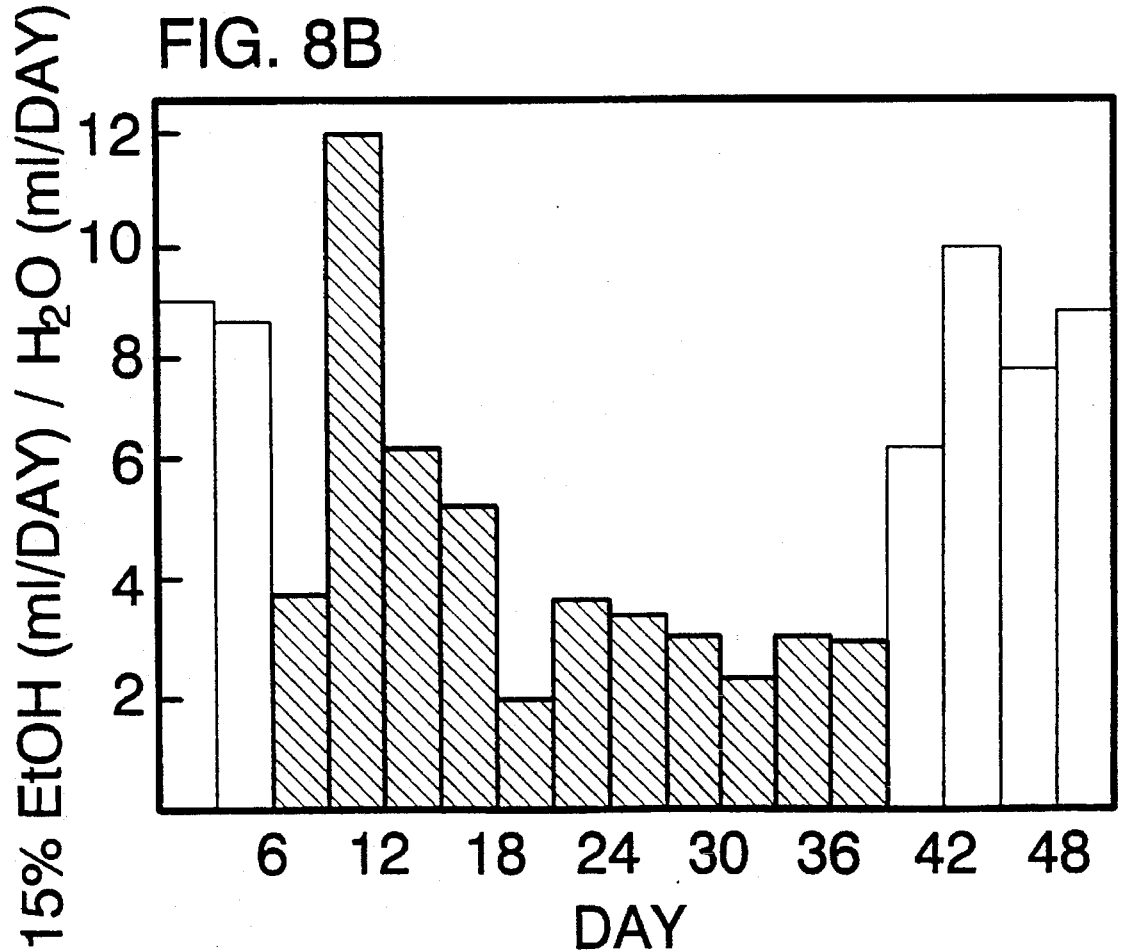
FIG. 8(B) is a histogram showing the effect of Radix Puerariae (RP) extract on free choice ethanol intake in golden hamsters.

As a control, the animals were then fed with 0.2 ml water twice daily, using a stainless steel animal feeding needle. Water feeding did not seem to have any effect on the animals' drinking behavior as measured by total fluid intake (FIG. 8a). After 6 days, the same group of hamsters were fed with 0.2 ml of RP extract (containing 1.6 mg of daidzin as analyzed by HPLC) twice daily. The extract had a dramatic effect on the preference ratio of the hamsters. As shown in FIG. 8b, except for day 9–12, the preference ratios were substantially lower when the animals were on the RP extract regimen. At day 39, feeding of RP extract was terminated and the preference ratio returned to normal. While RP had a dramatic effect on preference ratio (FIG. 8b), the total fluid intake was not affected (FIG. 8a).

EXAMPLE 5

In Vivo Effects of Daidzin on Alcohol Consumption

In order to demonstrate that daidzin decreases alcohol consumption in vivo, experiments were designed to test the effect of daidzin on free choice ethanol intake in golden hamsters. Hamsters were chosen as described in Example 4 based on previous reports that they display high ethanol intake and preference in comparison with several other mammalian species, and that this was correlated with differences in ethanol metabolism. Kulkosky and Cornell, 1979, supra.

The animals used in these experiments are adult male golden hamsters (outbred, Lakeview Lak: LVG[SYR]), purchased from Charles River Laboratories, Wilmington, Mass. 01887. Upon arrival, hamsters are housed (4 per cage) with ad libitum access to food and tap water in a room maintained at 23° C. on a 12/12 light/dark cycle (light on 0600–1800 hr.) for 1 week. Following this acclimation period, each hamster is transferred to an individual stainless steel metabolic cage (26×18×17.5 cm) with a wire mesh floor for the remainder of the experiment. Each cage is equipped with a stainless steel food hopper located on the right side of the front wall which was kept filled with food. Two 50 ml drinking bottles fitted with stainless steel sipper tubes are placed on the left side of the front wall. Under the sipper tubes are funnels which collect and direct spillage to tubes placed outside of the cages. Fluids are provided mainly during the dark cycle (1800–0800 hr.) and fluid intake is measured in the morning at the same time each day, for example, at 0800 hr. During this baseline period, for example, 8 days, two drinking solutions are provided for each animal. One is tap water; the other is a 30% v/v solution of ethanol (100% USP). The position of the two drinking bottles on each cage is alternated daily to prevent the development of positional preference. Hamsters that drink significant amounts of ethanol solution, for example more than 5 ml/day, and that display consistent water and ethanol consumption are selected for daidzin administration after the pretreatment period.

Figure 9A:
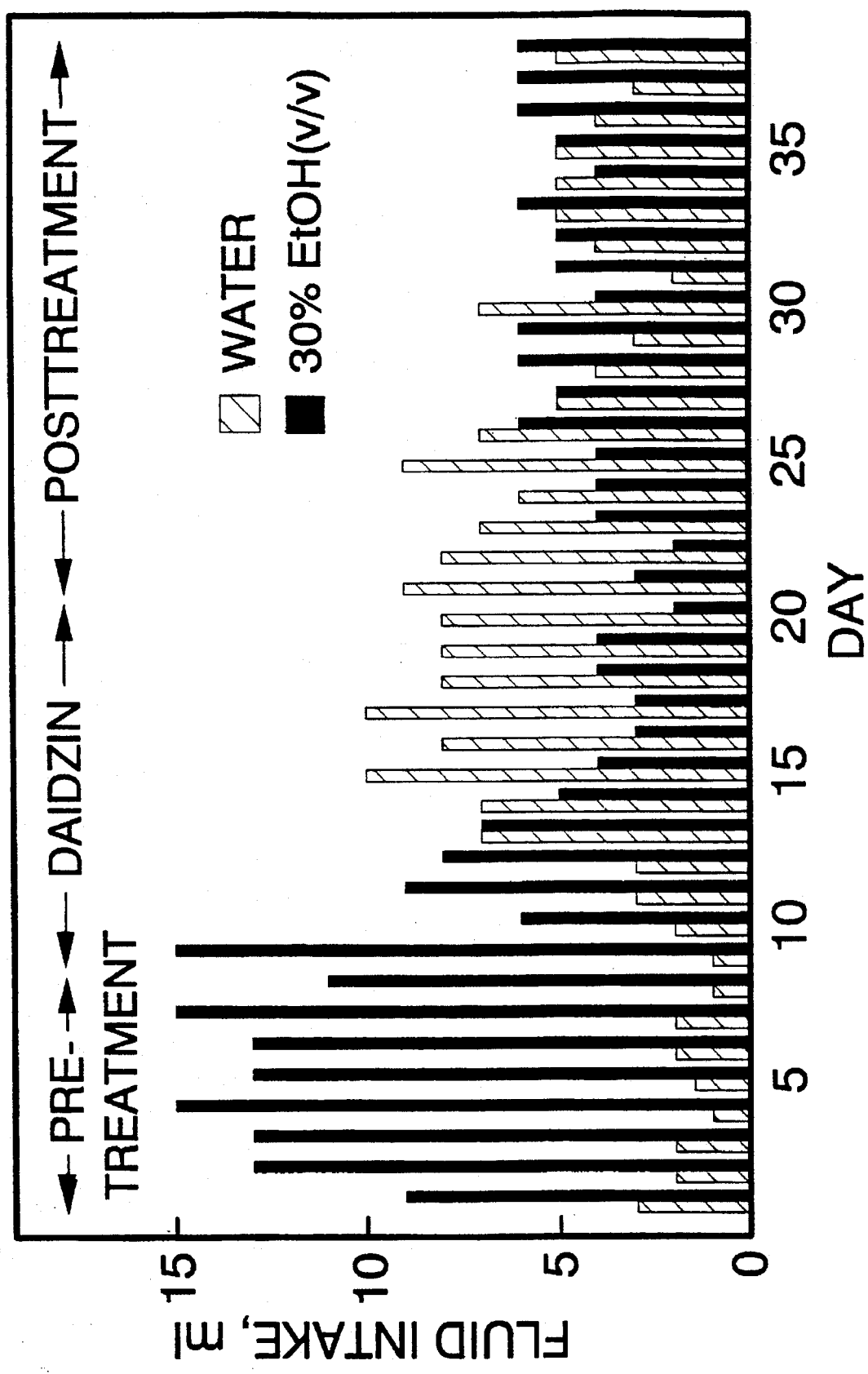
FIG. 9(A) is a histogram showing the effect of daidzin on free choice ethanol intake in golden hamster-6.

In one experiment, two of eleven hamsters tested during a pretreatment period of 8 days drank more than 5 ml of ethanol solution per day and displayed the most consistent water and ethanol consumption. These two were selected on the last day (day 8) of the pretreatment period for the study of the effect of daidzin. One of them (Number 6) exhibited a strong preference for ethanol solution (ethanol vs. water intake ratio 7.6); the other hamster (Number 9) displayed virtually no preference between water and ethanol solution (ethanol vs. water intake ratio 1.1) (FIGS. 9a,b).

Figure 9B:
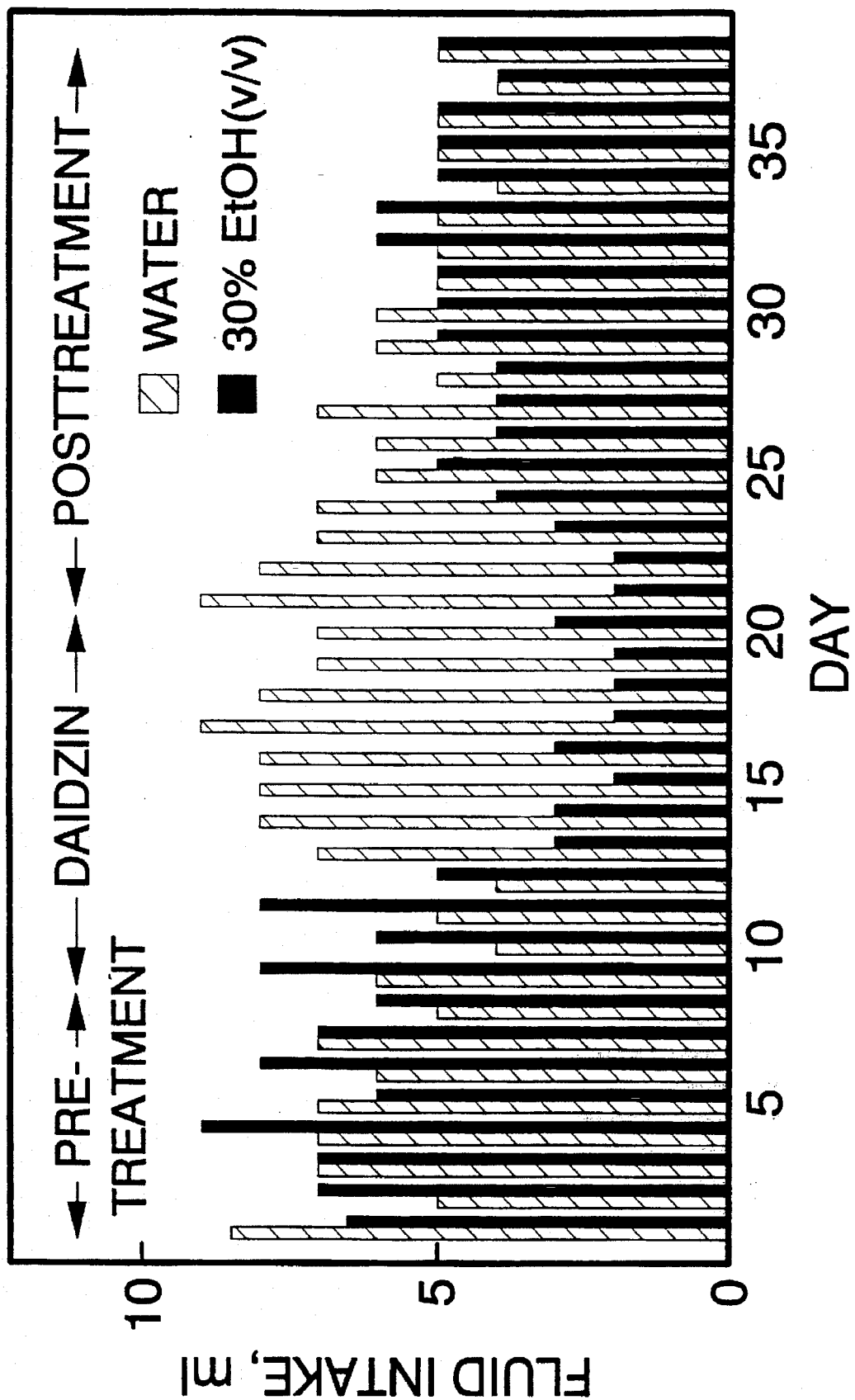
FIG. 9(B) is a histogram showing the effect of daidzin on free choice ethanol intake in golden hamster-9.

In this experiment, at 0900 hr. of day 9, the two hamsters selected (Numbers 6 and 9) received a single dose of 10 mg daidzin (as a 0.5 mL suspension in saline, subcutaneously) and in the following 13 days, each hamster was fed daily at 1700 hr. 10 mg of daidzin suspended on 0.5 mL water, using a stainless steel animal feeding needle. In other experiments, subcutaneous administration is preferably omitted, and each hamster receives only daily oral administration by feeding as described herein. As shown in FIG. 9a, alcohol intake by hamster Number 6 started to decline 2 days after the first dose of daidzin. This decline in alcohol intake was accompanied by a concomitant increase in water intake. While the total fluid intake was slightly decreased during the period of daidzin administration, more importantly, the total $H_2O$ intake, that is, the sum of water from the water bottle and water in the ethanol mixture, stayed nearly constant. A similar result was observed in hamster Number 9 except that in this animal, the effect of daidzin did not become apparent until the fourth day after the first dose was given as shown in FIG. 9b. Feeding of daidzin was terminated at 1700 hr. on day 20. The nearly constant and low ethanol preference ratios that characterized the last 70 to 75% of the treatment phase and the first two days of the posttreatment phase (Number 6, 0.40±0.04 SEM, days 14 to 22; Number 9, 0.31±0.02 SEM, days 13 to 22) increase significantly for the balance of the posttreatment phase approximately to the level of no preference for ethanol or water (Number 6, 1.19±0.11 SEM, days 23 to 38; Number 9 0.89±0.05 SEM, days 23 to 38).

In our experience, golden hamsters obtained from various U.S. sources undergo a cyclic change in alcohol preference. Specifically, in our experience, eighty to ninety percent of hamsters received from May through September did not prefer ethanol solutions, whereas at other times of the year nearly all hamsters showed a strong preference for ethanol. We are not aware of previous reports of this behavior in the literature. All hamsters in this and following examples of drinking behavior, except for Example 9, were preselected for alcohol preference, as described in Example 4.

During May to September, in those cases where no hamsters were found to prefer ethanol by free choice as described in Example 4, it was generally possible to train some of them to prefer ethanol by providing a 20% ethanol solution and no water for 10 to 20 days, after which they showed their trained preference for ethanol under free choice conditions. Such animals were used for the experiments described in Example 9. This methodology is commonly used to train outbred rats to consume ethanol (see, e.g., Samson, et al., 1988, Alcoholism: Clin. Exp. Res. 12:591–598).

EXAMPLE 6

Dose Effects on Alcohol Consumption of Daidzin Administered as a Pure Compound and as a Component of Crude RP Extract It is common practice in quantitative drug studies with rodents to use intraperitoneal (i.p.) administration to deliver drug doses accurately (Goodman and Gilman, 1975, *The Pharmacological Basis of Therapeutics*, 5th ed., Macmillan, N.Y., p. 8). In particular, this method avoids variability introduced by technical difficulties of oral administration via feeding (full versus empty stomach, etc.), variations in drug transport in the gastrointestinal tract (variations in intestinal fauna and flora, individual variations in absorption rate expected of outbred animals, etc.) and other factors. Hence, a quantitative dose effect experiment was performed as in Example 5 but with daidzin as the drug injected i.p. as a suspension in 1 ml of sterile saline. As a control 1 ml of sterile saline was injected i.p. daily during the baseline period (typically 7–9 days) that establishes drinking preference without the drug. Saline injection i.p. had no effect on the drinking behavior of golden hamsters. Ethanol was provided as a 20% solution. Hamsters could be used more than once (but were not used more than three times) in a cycle of baseline saline injections followed by drug injections, each cycle with the drug at a different dose.

The response to daidzin treatment was computed as:

$$\% \text{ Response} = (V_o - V_d) \times 100 / V_o$$

where $V_o$ is average daily intake of 20% ethanol during the baseline period and $V_d$ is the average daily intake during the daidzin treatment period.

Figure 10:
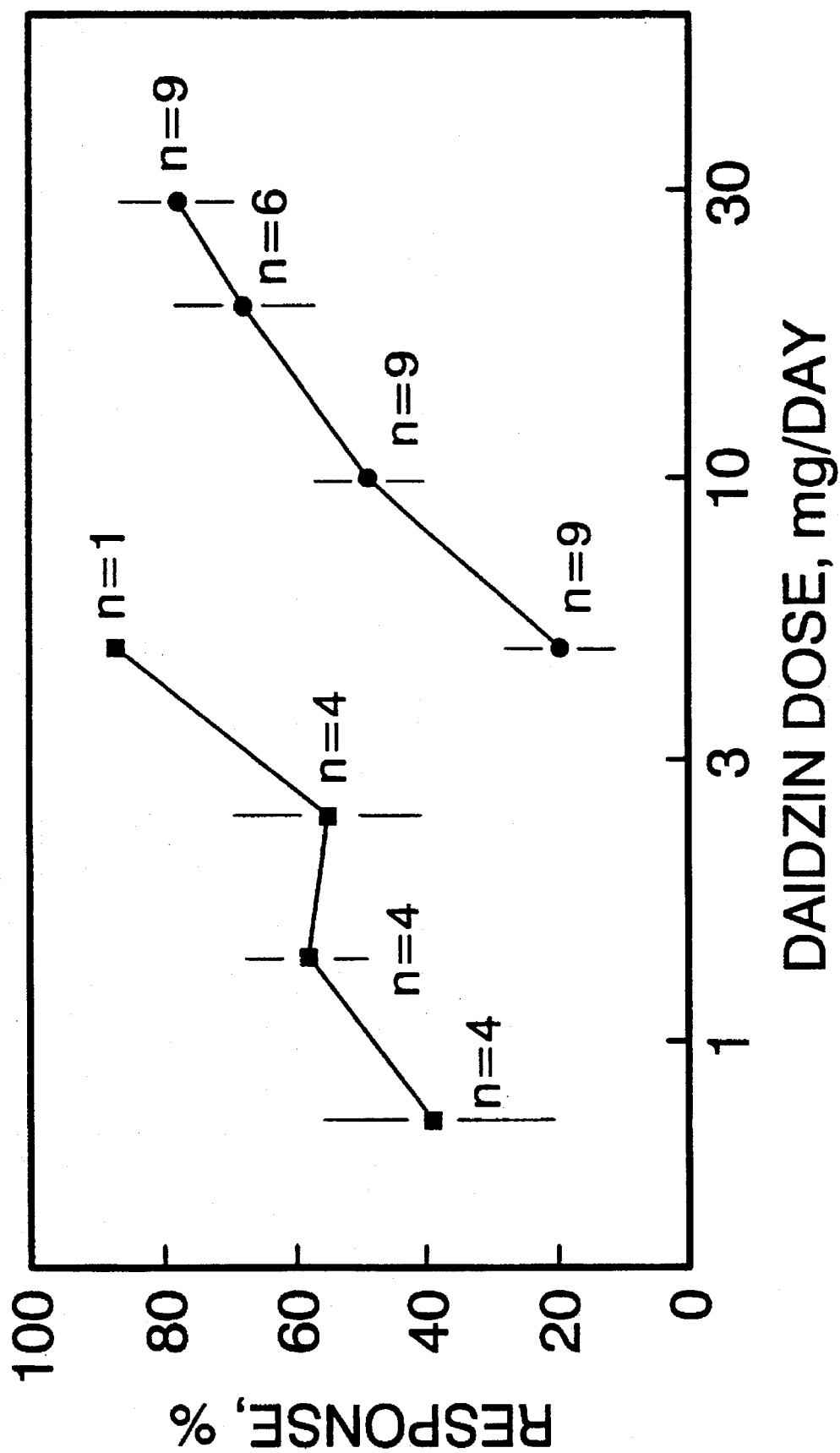
FIG. 10 is a graph showing the effect of varying doses (mg/day) of crude RP extract (solid squares) or pure synthetic daidzin (solid circles) on free choice ethanol intake in golden hamsters, as measured by percent suppressive response.

The right-hand curve of FIG. 10 (solid circles) shows a graded-dose response of pure daidzin on golden hamster alcohol intake. Data in the semilog plot are shown as mean±SE for 6 to 9 different determinations. The slope is typical of dose response curves. Daidzin at a dose of 5 mg/day suppresses hamster alcohol intake by 20%; suppression increases to 50% (i.e., $EC_{50}$ or half-maximal response) at 10 mg/day and increases further to 80% at 30 mg/day.

When this experiment was repeated with crude RP methanolic extract instead of pure daidzin the dose-response curve for daidzin in the crude extract was shifted left from the curve for pure daidzin as shown in the left-hand curve of FIG. 10 (solid squares) to an $EC_{50}$ value 5 to 10 times lower than that for pure daidzin. Hence, daidzin in the crude extract is 5 to 10 times more potent than pure daidzin. Among the possible explanations for this effect are any combination of the following: crude RP extract may contain additional active principle(s) that may act either additively or synergistically with daidzin in suppressing alcohol intake; or additional principle(s) in the crude RP extract may increase the bioavailability of daidzin and may act for example, by promoting its absorption intraperitoneally and/ or its transport across biomembranes generally. As demonstrated in the following example, the RP extract contains a factor or factors which increase the bioavailability of daidzin as determined by the administration of daidzin in the extract as compared with administration of purified daidzin.

EXAMPLE 7

Relative Bioavailability of Daidzin: Pure Daidzin vs Daidzin in Crude RP Extract In hamsters, daidzin administered i.p. as a crude RP extract has a higher relative bioavailability than pure daidzin as demonstrated in the following experiment.

Figure 11:
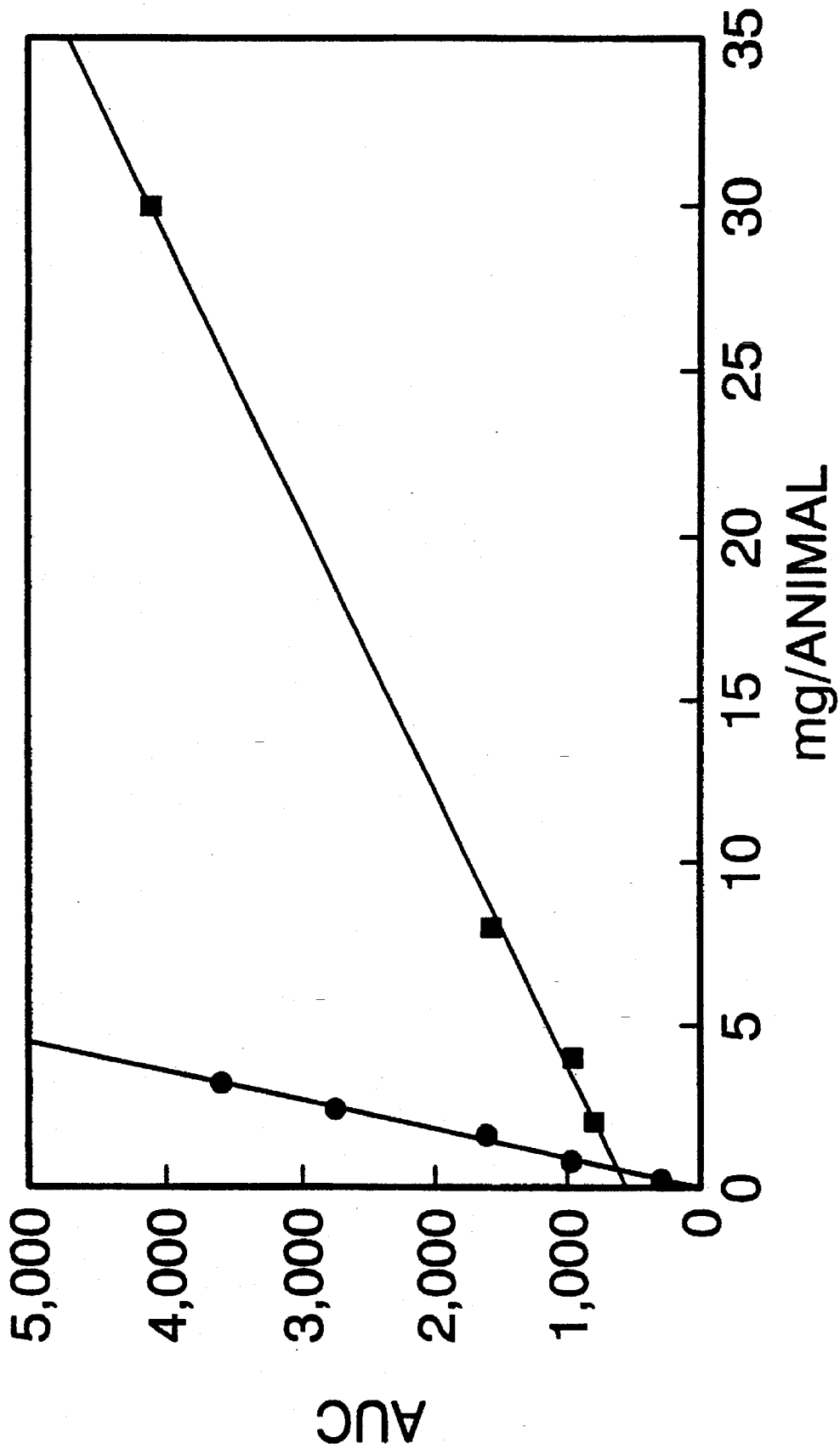
FIG. 11 is a graph showing the relative bioavailability (AUC) of varying doses (mg/animal) of daidzin administered as a crude RP extract (solid circles) or as pure daidzin (solid squares) in a golden hamster. AUC is a measure of relative bioavailability and quantitated as the area under the curve of the daidzin component present in plasma from a blood sample as measured by HPLC; this correlates with the actual amount of daidzin administered.
Figure 12:
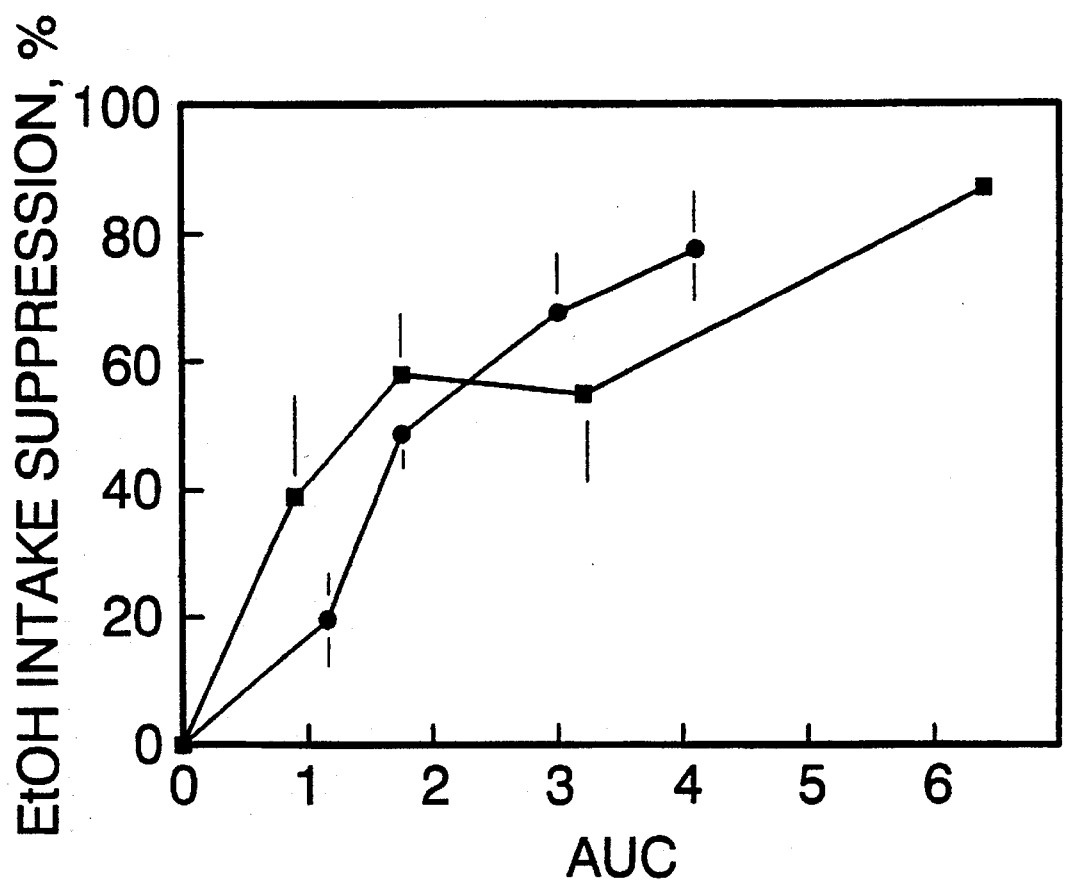
FIG. 12 is a graph showing the correlation between the (i) relative bioavailability (AUC, arbitrary unit) of varying doses of daidzin administered as a crude RP extract (solid squares) or as pure synthetic daidzin (solid circles) and (ii) the percent ethanol intake suppression response in a golden hamster.

Nine hamsters (130±10 g) were partially anesthetized with 1 mL of 30% ethanol i.p., and 30 min later, four of these were injected i.p. with different doses (2, 4, 8 or 30 mg) of pure daidzin suspended in 1 mL sterilized saline. The remaining five received different doses (30, 100, 200, 300 or 400 mg) of crude extract containing 0.24, 0.8, 1.6, 2.4 or 3.2 mg of daidzin in the same fashion. Blood samples, taken at intervals from the orbital venosus plexus, were collected in heparinized tubes. Plasma was obtained by centrifugation at 90000 rpm in a Beckman Airfuge. Plasma proteins were precipitated with an equal volume of acetonitrile and removed by centrifugation. The daidzin content of the supernatant solution was analyzed by HPLC. Plasma daidzin concentration-time curves were constructed from these data and the area under curve (AUC) in µM.min was estimated and defined as relative bioavailability. The relative bioavailability as shown in FIG. 11 of daidzin given in the form of crude extract (solid circles) is about 9 times that of daidzin administered as a pure compound (solid squares). When the dose-response curves of FIG. 10 were replotted using relative bioavailability rather than the daidzin doses given, the two curves virtually merged as shown by FIG. 12. In FIG. 12, the curve for daidzin administered as crude extract is represented by solid squares, whereas the curve for purified daidzin is represented by solid circles. These results not only indicate that daidzin in the crude RP extract is more readily available to the animal system, but also lends support to the proposal that daidzin is the major, if not the only, active principle in RP that suppresses alcohol intake. The increased bioavailability of daidzin given as the crude RP extract appears to be due to a factor or factors in the extract. Such a factor or factors may act by promoting solubility of daidzin in aqueous solution. For example, a saturated water solution of pure daidzin is 0.2 mM whereas a saturated water solution of previously dried RP methanolic extract, or of previously dried RP 95% ethanolic extract prepared as for the RP methanolic extract, is 7 mM in daidzin.

The following pharmaceutical solubilizing agents, obtained from Sigma Chemical Co., St. Louis, Mo., also increased the solubility of daidzin in water. Daidzin was highly soluble both in glycerol and in polyethylene glycol 400 (PEG). When a concentrated solution of daidzin in PEG was diluted with water to 20% PEG/$H_2O$, daidzin solubility was 4.5 mM. When β-cyclodextrin is dissolved in the above solution of daidzin in PEG at a concentration that yields 20 mg/ml of β-cyclodextrin after dilution to 20% PEG/$H_2O$, daidzin solubility was 9.4 mM. The solubility of daidzin in 10% aqueous polyvinylpyrrolidone 40 and in a saturated solution of a representative saponin, digitonin, was about 2 mM.

Different strategies may be employed to increase the bioavailability of drugs, of which several examples are given. These include making derivatives (i.e., analogs) of higher water solubility as in Example 8, using agents known to increase water solubility of drugs, e.g., polyethylene glycol, cyclodextrin, polyvinylpyrrolidone, saponins, etc., and/or isolating new agents, particularly from the RP extract, that increase water solubility of daidzin specifically or isoflavones or flavones in general.

EXAMPLE 8

Inhibition of ALDH by Novel Compounds Related to Daidzin

Novel compounds derived from daidzein (i.e., daidzin analogs) by reaction with various ω-bromo fatty acids or with ethyl iodide have been found unexpectedly to mimic the inhibitory properties of daidzin. These novel compounds are named as ethers of the 7-hydroxyl group of the aglycone daidzein; they resemble daidzin in that there is no free hydroxyl at the 7-position, but differ in that the daidzin glucosidic group is an acetal rather than an ether.

Daidzein (10 mmoles) was suspended in 40 ml of acetone, 10 ml of 2N KOH was added, followed by 10 mmoles of solid ω-bromohexanoic acid, ω-bromoheptanoic acid, ω-bromoundecanoic acid or ethyl iodide. The mixture was stirred under reflux for 3 days.

The potassium salt of the 7-(ω-carboxyalkyl) ether of daidzein was recovered by filtration, washed with acetone and dried; yield, 20–35%. The resultant white crystals were more than 95% pure and contained only about 1% daidzein as a contaminant, as determined by HPLC on a Waters radial pack C18, 5 µm, 0.8×10 cm column with a linear 15-min gradient elution from 0.1% trifluoroacetic acid to 80% acetonitrile/0.1% trifluroacetic acid at 1 mL/min monitored at 254 nm. Unreacted daidzein was the principal isoflavone component of the filtrate and can be recovered by acidification, filtration and recrystallization from ethanol. Retention times in the above HPLC system were: daidzin 13.92, daidzein 15.33, daidzein 7-(ω-carboxypentyl) ether 17.67, daidzein 7-(ω-carboxyhexyl) ether 18.27 and daidzein 7-(ω-carboxydecyl) ether 20.37 min. The longer retention times of the novel compounds are consistent with their lower polarity. Mass spectral analysis, performed as in Example 1, revealed molecular ion peaks at m/z 368 for the carboxypentyl derivative and at m/z 382 for the carboxyhexyl derivative. Daidzein peaks from decomposition of the molecular ions, at m/z 118, 137, 253 and 254 (Ganguly and Sarre, 1970, supra) were also evident. Ultraviolet absorption spectra of daidzein 7-(ω-carboxyhexyl) ether at pH 7.4 showed maxima at 250 and 304 nm, and no maximum at 331 nm that is characteristic of a free 7-hydroxyl group in daidzein. The spectrum at pH 11 showed maxima at 245, 250 and 280 nm characteristic of alkylation of the 7-OH group of daidzein as occurs in daidzin; daidzein at this pH has easily distinguishable maxima at 331 and 260 nm. The monopotassium salts of the carboxyalkyl derivatives were more soluble in water than was daidzin (0.2 mM): daidzein 7-(ω-carboxypentyl) ether 26 mM, daidzein 7-(ω- carboxyhexyl) ether 13 mM, daidzein 7-(ω-carboxydecyl) ether 9 mM. The free acids precipitated when the pH was adjusted to 2 with 1N HCl. Methanol was added to each of the suspensions, which were heated until the precipitates dissolved. Upon cooling white crystals of daidzein 7-(ω-carboxypentyl) ether mp 223–225 and daidzein 7-(ω-carboxyhexyl) ether mp 193–198 formed, whereas daidzein 7-(ω-carboxydecyl) ether separated as an oil.

The $H^1$ NMR spectra of the carboxypentyl and carboxyhexyl compounds in $d_6$-DMSO exhibited the high field resonances above 6 ppm expected for daidzin but not daidzein, as shown in Example 3. In the low field region there were multiplet resonances between 1.1 and 2.3 ppm that corresponded to 4 methylene groups in the carboxypentyl derivative and 5 in the carboxyhexyl derivative and a triplet at 4.1 ppm corresponding to two methylene protons adjacent to the ether linkage.

Daidzein 7-ethyl ether was obtained as a byproduct of the synthesis of daidzein by condensation of the hydroxyphenyl hydroxybenzyl ketone with ethyl orthoformate (Iyer et al., 1951, Proc. Ind. Acad. Sci. 33A:116). This byproduct has not been previously recognized or reported. An analogous byproduct has been reported in the synthesis of 7-ethoxyisoflavone (Mester et al., 1991, Chem. Abstract 115:158826b, Hung. Teljes HU 55,376 Abstract). The identity of the novel byproduct of the above ethy iodide reaction was established by HPLC; the retention time was 17.83 min. The byproduct exhibited the expected molecular ion peak at m/z 282 and daidzein-related peaks at 118, 137, 253 and 254. Ultraviolet spectra at pH 7.4 (maxima 250 and 304 nm) and pH 11 (245, 250 and 280 nm) were consistent with alkylation of the 7-OH position and not the 4'-OH position of daidzein.

The progress curve method described by Klyosov and Berezin, 1972, Biokhimiya (Engl. transl.), Plenum, New York, 37:141–151, was used instead of the initial velocity method of Example 3 to obtain precise values for inhibition constants for ALDH-I with acetaldehyde as substrate and the very tight binding novel inhibitors (Table VI).

TABLE VI

Competitive Inhibition of ALDH Isozymes by Daidzin and Analogs with Acetaldehyde as Substrate

| | $K_i$, nM | |
|---|---|---|
| | ALDH-I | ALDH-II |
| Daidzin | 42 | 28000 |
| Daidzein 7-ethyl ether | 38 | 440 |
| Daidzein 7-(ω-carboxypentyl) ether | 9 | 450 |
| Daidzein 7-(ω-carboxyhexyl) ether | 9 | 215 |
| Daidzein 7-(ω-carboxydecyl) ether | 3 | 185 |

All of the novel compounds are as potent as, or more potent than daidzin as inhibitors of ALDH-I, and all are selective for ALDH-I over ALDH-II, but none is as selective as daidzin: the ratio $K_{i, ALDH-II}/K_{i, ALDH-I}$ is 667 for daidzin, but is 24–62 for the carboxyalkyl derivatives.

EXAMPLE 9

In Vivo Effects of Daidzein 7-(ω-Carboxyhexyl) Ether and Daidzein 7-(ω-Carboxypentyl) Ether on Alcohol Consumption Daidzein 7-(ω-carboxyhexyl) ether and daidzein 7-(ω-carboxypentyl) ether also suppress alcohol intake in vivo. The experimental procedure was the same as for Example 6 except that trained hamsters described in Example 5 were used and the carboxyalkyl ether derivatives were tested at only one dose, 10 mg/day, which is the $EC_{50}$ for daidzin. At that dose daidzein 7-(ω-carboxyhexyl) ether suppresses golden hamsters alcohol intake by 72% and 69% in two hamsters (E23 and B7, respectively), and daidzein 7-(ω-carboxypentyl) ether suppresses intake by 72% and 56% in two hamsters (D6 and C14, respectively). Assuming a dose response slope similar to that of daidzin, both carboxyalkyl derivatives are not more than twice as potent as daidzin, which is within the range of experimental error.

EXAMPLE 10

Relative Bioavailability: Daidzin vs. Daidzein 7-(ω-Carboxyhexyl) Ether

Figure 13:
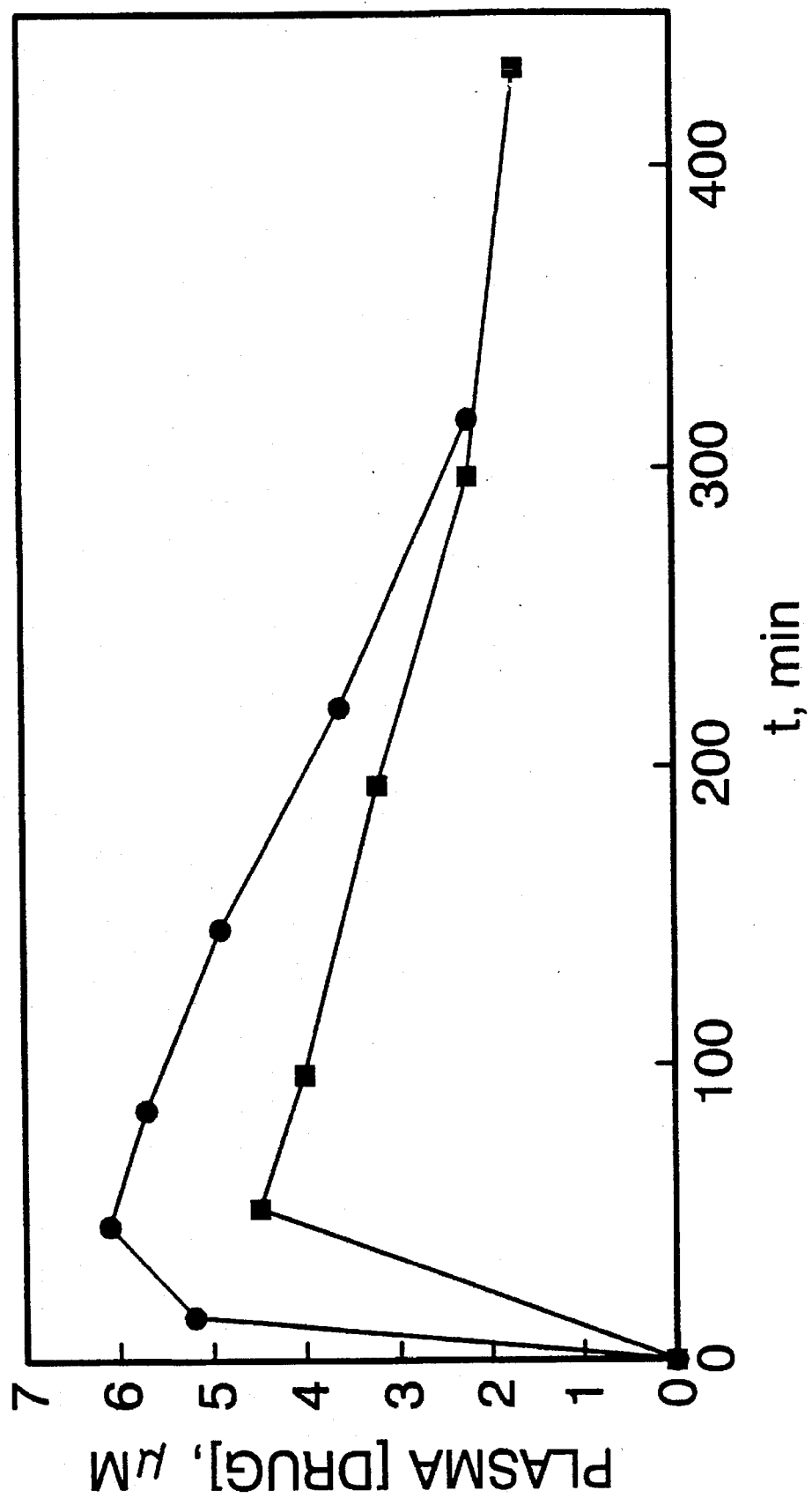
FIG. 13 is a graph showing the plasma drug concentration (in micromoles/liter) versus time (in minutes) for a single 10 mg dose synthetic daidzin (solid circles) or daidzein 7-($\omega$-carboxyhexyl) ether (designated "hepzein", solid squares) administered to a golden hamster.

The drug-time curves as shown in FIG. 13 for daidzein 7-(ω-carboxyhexyl) ether (solid squares) and daidzin (solid circles) in plasma, determined according to the same procedure as in Example 7 but at doses of 10 mg for each hamster, are also very similar to each other. Both compounds reached their maximal plasma concentrations (4.5 and 6 μM for the carboxyhexyl ether and daidzin, respectively) within about an hour after injection. Five hours later the plasma concentrations of both inhibitors were still above 2 μM, far above their competitive inhibition constants for ALDH-I.

What is claimed is:

1. A method for therapeutically treating alcohol consumption in a human comprising administering a pharmaceutical composition comprising daidzin in an effective amount to reduce alcohol consumption and a pharmaceutical carrier.

2. A method according to claim 1 wherein the composition induces a sensitivity reaction after alcohol consumption.

3. A method according to claim 1 wherein the human is an alcoholic.

4. The method of claim 1 wherein the effective amount is between about 0.1 mg to about 140 mg per kilogram of body weight.

5. A method for therapeutically treating alcohol consumption in a human comprising administering an amount of daidzin effective to reduce alcohol consumption.

6. The method of claim 5 wherein the amount of daidzin effective to reduce alcohol consumption is between about 0.1 mg to about 140 mg per kilogram of body weight.

* * * * *